US006947788B2

(12) United States Patent
Gilboa et al.

(10) Patent No.: US 6,947,788 B2
(45) Date of Patent: Sep. 20, 2005

(54) NAVIGABLE CATHETER

(75) Inventors: Pinhas Gilboa, Haifa (IL); Danny Blecher, Ramat Gan (IL)

(73) Assignee: Super Dimension Ltd., Herzelia (IL)

( * ) Notice: Subject to any disclaimer, the term of this patent is extended or adjusted under 35 U.S.C. 154(b) by 777 days.

(21) Appl. No.: 09/879,109

(22) Filed: Jun. 13, 2001

(65) Prior Publication Data

US 2002/0042571 A1 Apr. 11, 2002

Related U.S. Application Data

(62) Division of application No. 09/463,177, filed on Jan. 21, 2000.

(30) Foreign Application Priority Data

| Aug. 2, 1998 | (IL) | ................................................ 125626 |
| Oct. 29, 1998 | (IL) | ................................................ 126814 |
| Jul. 7, 1999 | (WO) | ................................ PCT/IL99/00371 |

(51) Int. Cl.⁷ ................................................ A61B 6/00
(52) U.S. Cl. ...................... 600/435; 600/407; 600/433; 600/437; 600/459; 600/466
(58) Field of Search ................................ 600/435, 407, 600/433, 437, 459, 466

(56) References Cited

U.S. PATENT DOCUMENTS

| 4,287,809 A | | 9/1981 | Egli et al. |
| 4,394,831 A | | 7/1983 | Egli et al. |
| 4,737,794 A | | 4/1988 | Jones |
| 4,742,356 A | | 5/1988 | Kuipers |
| 4,849,692 A | | 7/1989 | Blood |
| 4,945,912 A | * | 8/1990 | Langberg ..................... 600/374 |
| 5,347,289 A | | 9/1994 | Elhardt |
| 5,405,346 A | * | 4/1995 | Grundy et al. ................. 606/41 |
| 5,600,330 A | | 2/1997 | Blood |
| 5,713,369 A | * | 2/1998 | Tao et al. .................... 600/569 |
| 5,729,129 A | | 3/1998 | Acker |
| 5,752,513 A | | 5/1998 | Acker et al. |
| 5,752,518 A | * | 5/1998 | McGee et al. .............. 600/424 |
| 5,840,024 A | * | 11/1998 | Taniguchi et al. .......... 600/424 |
| 5,941,251 A | * | 8/1999 | Panescu et al. ............. 128/899 |
| 6,188,355 B1 | | 2/2001 | Gilboa |
| 6,304,769 B1 | * | 10/2001 | Arenson et al. ............ 600/424 |
| 6,585,763 B1 | * | 7/2003 | Keilman et al. ........... 623/1.42 |

FOREIGN PATENT DOCUMENTS

| WO | WO95/09562 | 4/1995 |
| WO | WO96/05768 | 2/1996 |
| WO | WO97/36143 | 10/1997 |

* cited by examiner

Primary Examiner—Eleni Mantis-Mercader
Assistant Examiner—William Jung
(74) Attorney, Agent, or Firm—Mark M. Friedman

(57) ABSTRACT

A catheter, including: a housing having a transverse inner dimension of at most about two millimeters; and a coil arrangement including five coils and five solid cores. Each of the coils is wound around one of the solid cores. The coils are non-coaxial. The coil arrangement is mounted inside the housing.

7 Claims, 20 Drawing Sheets

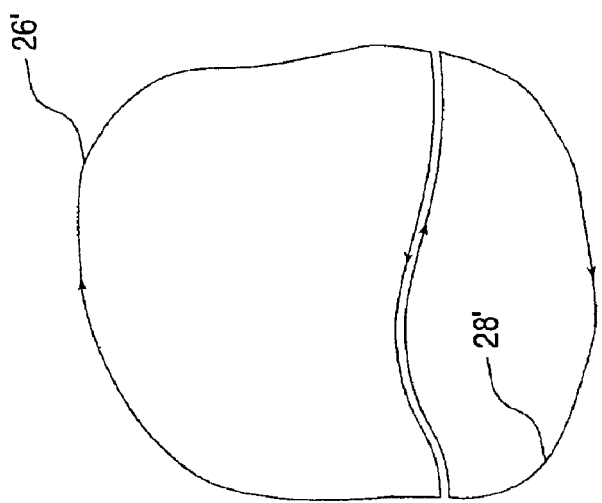
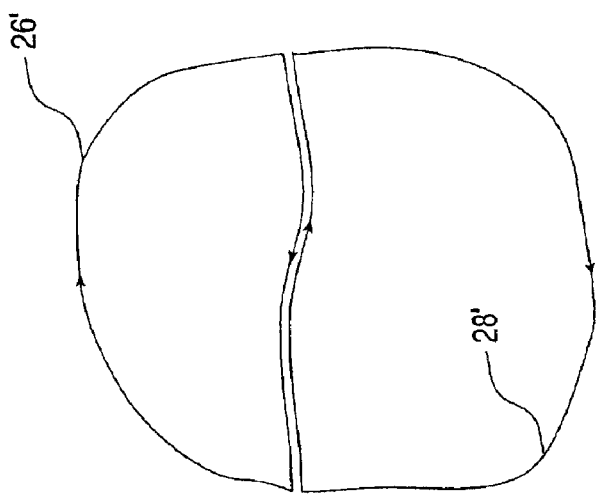
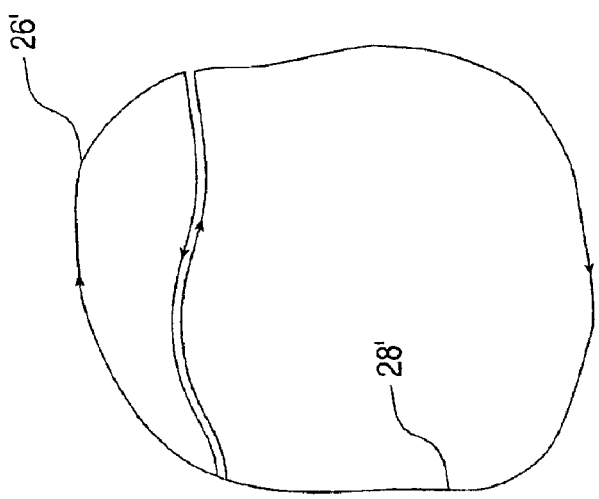

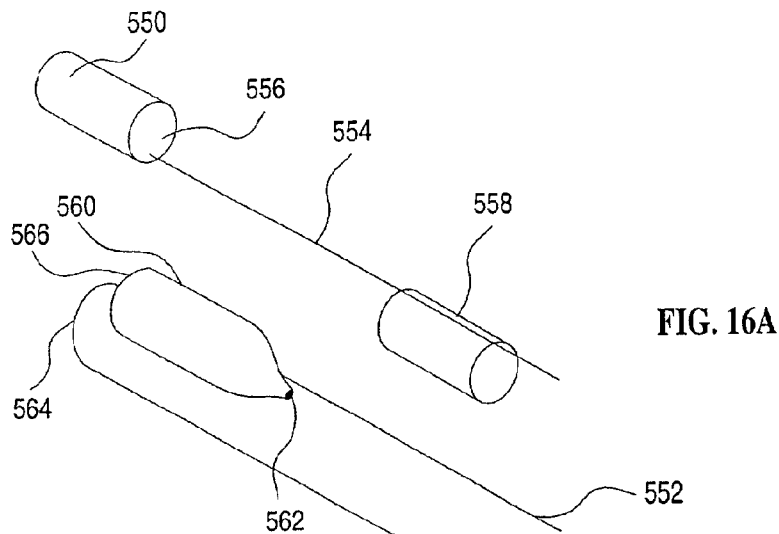
FIG. 16A
FIG. 16B
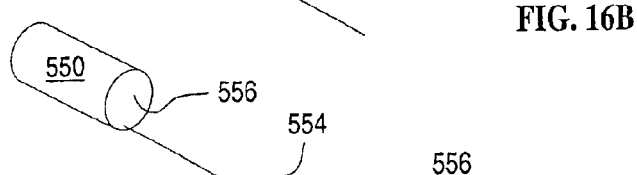
FIG. 16C
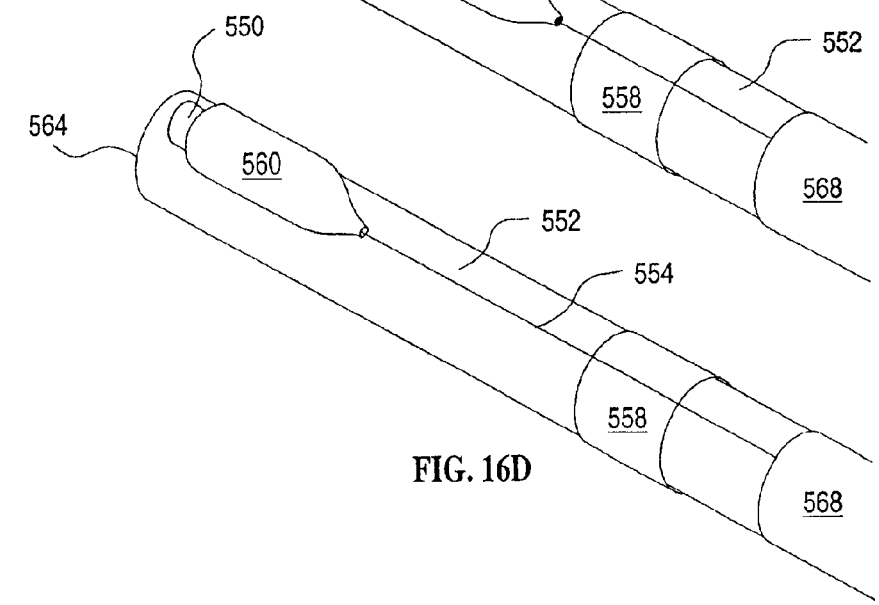
FIG. 16D

NAVIGABLE CATHETER

This is a Divisional of U.S. Ser. No. 09/463,177, filed Jun. 21, 2000.

FIELD AND BACKGROUND OF THE INVENTION

The present invention relates to electromagnetic tracking devices and, more particularly, to a system and method for tracking a medical probe such as a catheter as the probe is moved through the body of a patient.

It is known to track the position and orientation of a moving object with respect to a fixed frame of reference, by equipping the moving object with a transmitter that transmits electromagnetic radiation, placing a receiver in a known and fixed position in the fixed frame of reference, and inferring the continuously changing position and orientation of the object from signals transmitted by the transmitter and received by the receiver. Equivalently, by the principle of reciprocity, the moving object is equipped with a receiver, and a transmitter is placed in a known and fixed position in the fixed frame of reference. Typically, the transmitter includes three orthogonal magnetic dipole transmitting antennas; the receiver includes three orthogonal magnetic dipole receiving sensors; and the object is close enough to the stationary apparatus (transmitter or receiver), and the frequencies of the signals are sufficiently low, that the signals are near field signals. Also typically, the system used is a closed loop system: the receiver is hardwired to, and explicitly synchronized with, the transmitter. Representative prior art patents in this field include U.S. Pat. No. 4,287,809 and U.S. Pat. No. 4,394,831, to Egli et al.; U.S. Pat. No. 4,737,794, to Jones; U.S. Pat. No. 4,742,356, to Kuipers; U.S. Pat. No. 4,849,692, to Blood; and U.S. Pat. No. 5,347,289, to Elhardt. Several of the prior art patents, notably Jones, present non-iterative algorithms for computing the position and orientation of magnetic dipole transmitters with respect to magnetic dipole receivers.

An important variant of such systems is described in U.S. Pat. No. 5,600,330, to Blood. In Blood's system, the transmitter is fixed in the fixed reference frame, and the receiver is attached to the moving object. Blood's transmitting antennas are spatially extended, and so cannot be treated as point sources. Blood also presents an algorithm which allows the orientation, but not the position, of the receiver relative to the transmitter to be calculated non-iteratively.

Systems similar to Blood's are useful for tracking a probe, such as a catheter or an endoscope, as that probe is moved through the body of a medical patient. It is particularly important in this application that the receiver be inside the probe and that the transmitter be external to the patient, because transmitting antennas of sufficient power would not fit inside the confined volume of the probe. A representative prior art system of this type is described in PCT Publication WO 96/05768, entitled "Medical Diagnosis, Treatment and Imaging Systems", which is incorporated by reference for all purposes as if fully set forth herein. Medical applications of such systems include cismyocardial revascularization, balloon catheterization, stent emplacement, electrical mapping of the heart and the insertion of nerve stimulation electrodes into the brain.

Perhaps the most important application of this tracking is to intrabody navigation, as described by Acker in U.S. Pat. No. 5,729,129, with reference to PCT Publication No. WO 95/09562. A three-dimensional image, such as a CT or MRI image, of the patient is acquired. This image includes fiducial markers at predetermined fiducial points on the surface of the patient. Auxiliary receivers similar to the receiver of the probe are placed at the fiducial points. The signals received by the auxiliary receivers are used to register the image with respect to the transmitter frame of reference, so that an icon that represents the probe can be displayed, superposed on a slice of the image, with the correct position and orientation with respect to the image. In this way, a physician can see the position and orientation of the probe with respect to the patient's organs.

WO 96/05768 illustrates another constraint imposed on such systems by the small interior dimensions of the probe. In most prior art systems, for example, the system of Egli et al., the receiver sensors are three concentric orthogonal coils wound on a ferrite core. The coils are "concentric" in the sense that their centers coincide. Such a receiver of sufficient sensitivity would not fit inside a medical probe. Therefore, the sensor coils of WO 96/05768 are collinear: the three orthogonal coils are positioned one behind the other, with their centers on the axis of the probe, as illustrated in FIG. 3 of WO 96/05768. This reduces the accuracy of the position and orientation measurements, because instead of sensing three independent magnetic field components at the same point in space, this receiver senses three independent magnetic field components at three different, albeit closely spaced, points in space.

A further, consequent concession of the system of WO 96/05768 to the small interior dimensions of a catheter is the use of coils wound on air cores, rather than the conventional ferrite cores. The high mutual coupling of collinear coils wound on ferrite cores and measuring three independent field components at three different points in space would distort those measurements sufficiently to make those measurements fatally nonrepresentative of measurements at a single point.

Another drawback of the system of WO 96/05768 relates to the geometry of the transmitter antennas. These are three nonoverlapping flat coplanar coils, preferably arranged in a triangle. Because the strength of the field transmitted by one of these coils falls as the reciprocal cube of the distance from the coil, the receiver usually senses fields of very disparate strength, which further degrades the accuracy of the position and orientation measurements. Acker addresses this problem by automatically boosting the power supplied to transmitting coils far from the receiver. In U.S. Pat. No. 5,752,513, Acker et al. address this problem by overlapping the coplanar transmitting coils.

Acker et al. transmit time-multiplexed DC signals. This time multiplexing slows down the measurement. Frequency multiplexing, as taught in WO 96/05768, overcomes this problem, but introduces a new problem insofar as the transmitting coils are coupled by mutual inductance at non-zero transmission frequency, so that the transmitted field geometry is not the simple geometry associated with a single coil, but the more complex geometry associated with several coupled coils. This complicates and slows down the calculation of the position and orientation of the receiver relative to the transmitter coils. PCT Publication WO 97/36143, entitled "Mutual Induction Correction", addresses this problem by generating, at each transmitter coil, counterfields that cancel the fields generated by the other transmitter coils.

A further source of slowness in calculating the position and orientation of the receiver is the iterative nature of the calculation required for a spatially extended transmitter. As noted above, Blood calculates the position of the receiver iteratively. Even in the DC case, Acker et al. calculate both the position and the orientation of the receiver iteratively.

There is thus a widely recognized need for, and it would be highly advantageous to have, a faster and more accurate method for tracking a medical probe inside the body of a patient.

SUMMARY OF THE INVENTION

According to the present invention there is provided a system for tracking a position and an orientation of a probe, including a plurality of first sensors, each of the first sensors for detecting a different component of a vector force field, each of the first sensors including two sensor elements disposed symmetrically about a common reference point in the probe, the first sensors being mounted inside the probe.

According to the present invention there is provided a method for determining a position and an orientation of an object with respect to a reference frame, including the steps of: (a) providing the object with three independent sensors of electromagnetic radiation; (b) providing three independent transmitting antennas of the electromagnetic radiation, each of the transmitting antennas having a fixed position in the reference frame, at least one of the transmitting antennas being spatially extended; (c) transmitting the electromagnetic radiation, using the transmitting antennas, a first of the transmitting antennas transmitting the electromagnetic radiation of a first spectrum, a second of the transmitting antennas transmitting the electromagnetic radiation of a second spectrum independent of the first spectrum, and a third of the transmitting antennas transmitting the electromagnetic radiation of a third spectrum independent of the first spectrum; (d) receiving signals corresponding to the electromagnetic radiation, at all three of the sensors, at a plurality of times, in synchrony with the transmitting of the electromagnetic radiation; and (e) inferring the position and the orientation of the object noniteratively from the signals.

According to the present invention there is provided a system for determining a position and an orientation of an object, including: (a) a plurality of at least partly overlapping transmitter antennas; (b) a mechanism for exciting the transmitter antennas to transmit electromagnetic radiation simultaneously, the electromagnetic radiation transmitted by each of the transmitter antennas having a different spectrum; (c) at least one electromagnetic field sensor, associated with the object, operative to produce signals corresponding to the electromagnetic radiation; and (d) a mechanism for inferring the position and the orientation of the object from the signals.

According to the present invention there is provided a system for determining a position and an orientation of an object, including: (a) a plurality of at least partly overlapping transmitter antennas; (b) a mechanism for exciting each of the transmitter antennas to transmit electromagnetic radiation of a certain single independent frequency and phase, the mechanism including, for each of the transmitter antennas, a mechanism for decoupling the each transmitter antenna from the electromagnetic radiation transmitted by every other transmitter antenna; (c) at least one electromagnetic field sensor, associated with the object, operative to produce signals corresponding to the electromagnetic radiation; and (d) a mechanism for inferring the position and the orientation of the object from the signals.

According to the present invention there is provided a catheter, including: (a) a housing having a transverse inner dimension of at most about two millimeters; and (b) at least one coil, wound about a solid core, mounted inside the housing.

According to the present invention there is provided a system for navigating a probe inside a body, including: (a) a receiver of electromagnetic radiation, inside the probe; (b) a device for acquiring an image of the body; and (c) a transmitter, of the electromagnetic radiation, including at least one antenna rigidly attached to the device so as to define a frame of reference that is fixed with respect to the device.

According to the present invention there is provided a system for navigating a probe inside a body, including: (a) a first receiver of electromagnetic radiation, inside the probe; (b) a device for acquiring an image of the body; and (c) a second receiver, of the electromagnetic radiation, rigidly attached to the device so as to define a frame of reference that is fixed with respect to the device.

According to the present invention there is provided a method of navigating a probe inside a body, including the steps of: (a) providing a device for acquiring an image of the body; (b) simultaneously: (i) acquiring the image of the body, and (ii) determining a position and orientation of the probe with respect to the image; and (c) displaying the image of the body with a representation of the probe superposed thereon according to the position and the orientation.

According to the present invention there is provided a device for sensing an electromagnetic field at a point, including at least four sensing elements, at least two of the sensing elements being disposed eccentrically with respect to the point.

According to the present invention there is provided a method for determining a position and an orientation of an object with respect to a reference frame, including the steps of: (a) providing the object with three independent sensors of electromagnetic radiation; (b) providing three independent transmitting antennas of the electromagnetic radiation, each of the transmitting antennas having a fixed position in the reference frame, at least one of the transmitting antennas being spatially extended; (c) transmitting the electromagnetic radiation, using the transmitting antennas, a first of the transmitting antennas transmitting the electromagnetic radiation of a first spectrum, a second of the transmitting antennas transmitting the electromagnetic radiation of a second spectrum independent of the first spectrum, and a third of the transmitting antennas transmitting the electromagnetic radiation of a third spectrum independent of the first spectrum; (d) receiving signals corresponding to the electromagnetic radiation, at all three of the sensors, at a plurality of times, in synchrony with the transmitting of the electromagnetic radiation; (e) setting up an overdetermined set of linear equations relating the signals to a set of amplitudes, there being, for each of the sensors: for each transmitting antenna: one of the amplitudes; and (f) solving the set of linear equations for the amplitudes.

According to the present invention there is provided a method of navigating a probe inside a body, including the steps of: (a) providing a device for acquiring an image of the body; (b) simultaneously: (i) acquiring the image of the body, and (ii) determining a position and an orientation of the body with respect to the image; (c) determining a position and an orientation of the probe with respect to the body; and (d) displaying the image of the body with a representation of the probe superposed thereon according to both of the positions and both of the orientations.

According to the present invention there is provided a device for sensing an electromagnetic field at a point, including: (a) two sensing elements, each of the sensing elements including a first lead and a second lead, the first leads being electrically connected to each other and to ground; and (b) a differential amplifier, each of the second leads being electrically connected to a different input of the differential amplifier.

According to the present invention there is provided a catheter including: (a) an outer sleeve having an end; (b) an inner sleeve having an end and slidably mounted within the outer sleeve; (c) a first flexible member connecting the end of the outer sleeve to the end of the inner sleeve; and (d) a first coil mounted on the first flexible member.

According to the present invention there is provided a system for determining a position and an orientation of an object, including: (a) at least one transmitter antenna for transmitting an electromagnetic field; (b) a first electromagnetic field sensor, associated with the object and including two sensing elements responsive to a first component of the transmitted electromagnetic field, each of the sensing elements including a first lead and a second lead, the first leads being electrically connected to each other and to ground; and (c) a first differential amplifier, each of the second leads being electrically connected to a different input of the first differential amplifier.

According to the present invention there is provided an imaging device, including: (a) an electrically conducting surface; (b) a magnetically permeable compensator; and (c) a mechanism for securing the compensator relative to the surface so as to substantially suppress a distortion of an external electromagnetic field caused by the surface.

According to the present invention there is provided a device for sensing an electromagnetic field, including: (a) a housing, including a first pair of diametrically opposed apertures, (b) a first core mounted in the first pair of apertures; and (c) a first coil of electrically conductive wire wound about the core.

According to the present invention there is provided a probe for interacting with a body cavity, including: (a) a substantially cylindrical catheter; (b) a satellite; and (c) a mechanism for reversibly securing the satellite at a fixed position and orientation relative to the catheter after the catheter and the satellite have been inserted into the body cavity.

Each receiver sensor of the present invention includes two sensor elements placed symmetrically with respect to a reference point inside the probe. All the sensor element pairs share the same reference point, so that the measured magnetic field components are representative of the field component values at the single reference point, instead of at three different points, as in the prior art system, despite the confined transverse interior dimensions of the probe. Because of the symmetric disposition of the sensor elements with respect to the reference point, the measured magnetic field components are representative of the field components at the reference point, despite the individual sensing elements not being centered on the reference point. This property of not being centered on the reference point is termed herein an eccentric disposition with respect to the reference point.

In one preferred embodiment of the receiver of the present invention, the sensor elements are helical coils. Within each sensor, the coils are mutually parallel and connected in series. As in the case of the prior art receivers, the coils are arranged with their centers on the axis of the probe. To ensure that coils of different sensors are mutually perpendicular, the probe housing includes mutually perpendicular pairs of diametrically opposed apertures formed therein, the coils whose axes are perpendicular to the axis of the probe are wound about cores whose ends extend past the ends of the respective coils, and the ends of the cores are mounted in their respective apertures.

In another preferred embodiment of the receiver of the present invention, with three sensors, the sensor elements are flat rectangular coils bent to conform to the shape of the cylindrical interior surface of the probe. The sensor elements of the three sensors are interleaved around the cylindrical surface. The advantage of this preferred embodiment over the first preferred embodiment is that this preferred embodiment leaves room within the probe for the insertion of other medical apparati.

As noted above, within any one sensor, the coils are connected in series. This connection is grounded. The other end of each coil is connected, by one wire of a twisted pair of wires, to a different input of a differential amplifier.

In a preferred embodiment of a cardiac catheter that incorporates a receiver of the present invention, the catheter includes an inner sleeve mounted slidably within an outer sleeve. One of the sensors includes two coils mounted within the inner sleeve, towards the distal end of the catheter. The distal end of the inner sleeve is connected to the distal end of the outer sleeve by flexible strips. Each of the other sensors includes two coils mounted on opposed lateral edges of a pair of flexible strips that flank the inner sleeve, with the inner sleeve running between the two members of the pair. When the inner sleeve is in the extended position thereof relative to the outer sleeve, the flexible strips lie flat against the inner sleeve, and the catheter can be maneuvered towards a patient's heart via the patient's blood vessels. When the end of the catheter has been introduced to the targeted chamber of the heart, the inner sleeve is withdrawn to the retracted position thereof relative to the outer sleeve, and the pairs of flexible strips form circles that are concentric with the reference point. Also mounted on the outward-facing surfaces of the flexible strips and, optionally, on the distal end of the inner sleeve, are electrodes for electrophysiologic mapping of the heart. Alternatively, the electrode on the distal end of the inner sleeve may be used for ablation of cardiac tissue, for example in the treatment of ventricular tachycardia.

An alternative preferred embodiment of the cardiac catheter of the present invention has an inflatable balloon connecting the distal ends of the inner and outer sleeves. The coils of the external sensors are mounted on the external surface of the balloon. When the inner sleeve is in the extended position thereof relative to the outer sleeve, the balloon lies flat against the inner sleeve, and the catheter can be maneuvered towards the patient's heart via the patient's blood vessels. When the end of the catheter has been introduced to the targeted chamber of the heart, the inner sleeve is withdrawn to the retracted position thereof relative to the outer sleeve, and the balloon is inflated to a sphere that is concentric with the reference point.

Although the primary application of the receiver of the present invention is to tracking a probe by receiving externally generated electromagnetic radiation, the scope of the present invention includes receivers for similar tracking based on the reception of any externally generated vector force field, for example, a time varying isotropic elastic field.

The algorithm of the present invention for inferring the position and orientation of the receiver with respect to the transmitter is similar to the algorithm described in co-pending Israel Patent Application 122578. The signals received by the receiver are transformed to a 3×3 matrix M.

The columns of M correspond to linear combinations of the amplitudes of the transmitted fields. The rows of M correspond to the receiver sensors. A rotationally invariant 3×3 position matrix W and a 3×3 rotation matrix Tare inferred noniteratively from the matrix M. The Euler angles that represent the orientation of the receiver relative to the transmitter antennas are calculated noniteratively from the elements of T, and the Cartesian coordinates of the receiver relative to the transmitter antennas are calculated from the elements of W A preliminary calibration of the system, either by explicitly measuring the signals received by the receiver sensors at a succession of positions and orientations of the receiver, or by theoretically predicting these signals at the successive positions and orientations of the receiver, is used to determine polynomial coefficients that are used in the noniterative calculation of the Euler angles and the Cartesian coordinates. In essence, the extra time associated with an iterative calculation is exchanged for the extra time associated with an initial calibration. One simplification of the algorithm of the present invention, as compared to the algorithm of IL 122578, derives from the fact that the system of the present invention is a closed loop system.

The preferred arrangement of the transmitter antennas of the present invention is as a set of flat, substantially coplanar coils that at least partially overlap. Unlike the preferred arrangement of Acker et al., it is not necessary that every coil overlap every other coil, as long as each coil overlaps at least one other coil. The most preferred arrangement of the transmitter antennas of the present invention consists of three antennas. Two of the antennas are adjacent and define a perimeter. The third antenna partly follows the perimeter and partly overlaps the first two antennas. The elements of the first column of M are sums of field amplitudes imputed to the first two antennas. The elements of the second column of M are differences of field amplitudes imputed to the first two antennas. The elements of the third column of M are linear combinations of the field amplitudes imputed to all three antennas that correspond to differences between the field amplitudes imputed to the third antenna and the field amplitudes that would be imputed to a fourth antenna that overlaps the portion of the first two antennas not overlapped by the third antenna.

The signals transmitted by the various antennas of the present invention have different, independent spectra. The term "spectrum", as used herein, encompasses both the amplitude and the phase of the transmitted signal, as a function of frequency. So, for example, if one antenna transmits a signal proportional to cos ωt and another antenna transmits a signal proportional to sin ωt, the two signals are said to have independent frequency spectra because their phases differ, even though their amplitude spectra both are proportional to δ(ω). The term "independent spectra", as used herein, means that one spectrum is not proportional to another spectrum. So, for example, if one antenna transmits a signal equal to cosωt and another antenna transmits a signal equal to 2 cos ωt, the spectra of the two signals are not independent. Although the scope of the present invention includes independent transmitted signals that differ only in phase, and not in frequency, the examples given below are restricted to independent transmitted signals that differ in their frequency content.

The method employed by the present invention to decouple the transmitting antennas, thereby allowing each antennas to transmit at only a single frequency different from the frequencies at which the other antennas transmit, or, alternatively, allowing two antennas to transmit at a single frequency but with a predetermined phase relationship between the two signals, is to drive the antennas with circuitry that makes each antenna appear to the fields transmitted by the other antennas as an open circuit. To accomplish this, the driving circuitry of the present invention includes active circuit elements such as differential amplifiers, unlike the driving circuitry of the prior art, which includes only passive elements such as capacitors and resistors. By "driving circuitry" is meant the circuitry that imposes a current of a desired transmission spectrum on an antenna, and not, for example, circuitry such as that described in WO 97/36143 whose function is to detect transmissions by other antennas with other spectra and generate compensatory currents.

With respect to intrabody navigation, the scope of the present invention includes the simultaneous acquisition and display of an image of the patient and superposition on that display of a representation of a probe inside the patient, with the representation positioned and oriented with respect to the image in the same way as the probe is positioned and oriented with respect to the patient. This is accomplished by positioning and orienting the imaging device with respect to the frame of reference of the transmitter, in one of two ways. Either the transmitter antennas are attached rigidly to the imaging device, or a second receiver is attached rigidly to the imaging device and the position and orientation of the imaging device with respect to the transmitter are determined in the same way as the position and orientation of the probe with respect to the transmitter are determined. This eliminates the need for fiducial points and fiducial markers. The scope of the present invention includes both 2D and 3D images, and includes imaging modalities such as CT, MRI, ultrasound and fluoroscopy. Medical applications to which the present invention is particularly suited include transesophageal echocardiography, intravascular ultrasound and intracardial ultrasound. In the context of intrabody navigation, the term "image" as used herein refers to an image of the interior of the patient's body, and not to an image of the patient's exterior.

Under certain circumstances, the present invention facilitates intrabody navigation even if the image is acquired before the probe is navigated through the patient's body with reference to the image. A third receiver is attached rigidly to the limb of the patient to which the medical procedure is to be applied. During image acquisition, the position and orientation of the third receiver with respect to the imaging device is determined as described above. This determines the position and orientation of the limb with respect to the image. Subsequently, while the probe is being moved through the limb, the position and orientation of the probe with respect to the limb is determined using the second method described above to position and orient the probe with respect to the imaging device during simultaneous imaging and navigation. Given the position and orientation of the probe with respect to the limb and the orientation and position of the limb with respect to the image, it is trivial to infer the position and orientation of the probe with respect to the image.

Many imaging devices used in conjunction with the present invention include electrically conducting surfaces. One important example of such an imaging device is a fluoroscope, whose image intensifier has an electrically conducting front face. According to the present invention, the imaging device is provided with a magnetically permeable compensator to suppress distortion of the electromagnetic field near the electrically conducting surface as a consequence of eddy currents induced in the electrically conducting surface by the electromagnetic waves transmitted by the transmitting antennas of the present invention.

The scope of the present invention includes a scheme for retrofitting an apparatus such as the receiver of the present invention to a catheter to produce an upgraded probe for investigating or treating a body cavity of a patient. A tether provides a loose mechanical connection between the apparatus and the catheter while the apparatus and the catheter are inserted into the patient. When the apparatus and the catheter reach targeted body cavity, the tether is withdrawn to pull the apparatus into a pocket on the catheter. The pocket holds the apparatus in a fixed position and orientation relative to the catheter.

BRIEF DESCRIPTION OF THE DRAWINGS

The invention is herein described, by way of example only, with reference to the accompanying drawings, wherein:

FIGS. 7A, 7B and 7C show alternative configurations of paired adjacent loop antennas;

FIG. 16 illustrates a scheme for retrofitting an apparatus such as the receiver of FIG. 2A to a catheter.

DESCRIPTION OF THE PREFERRED EMBODIMENTS

The present invention is of a system and method for tracking the position and orientation of an object relative to a fixed frame of reference. Specifically, the present invention can be used to track the motion of a medical probe such as a catheter or an endoscope within the body of a patient.

The principles and operation of remote tracking according to the present invention may be better understood with reference to the drawings and the accompanying description.

Figure 1:
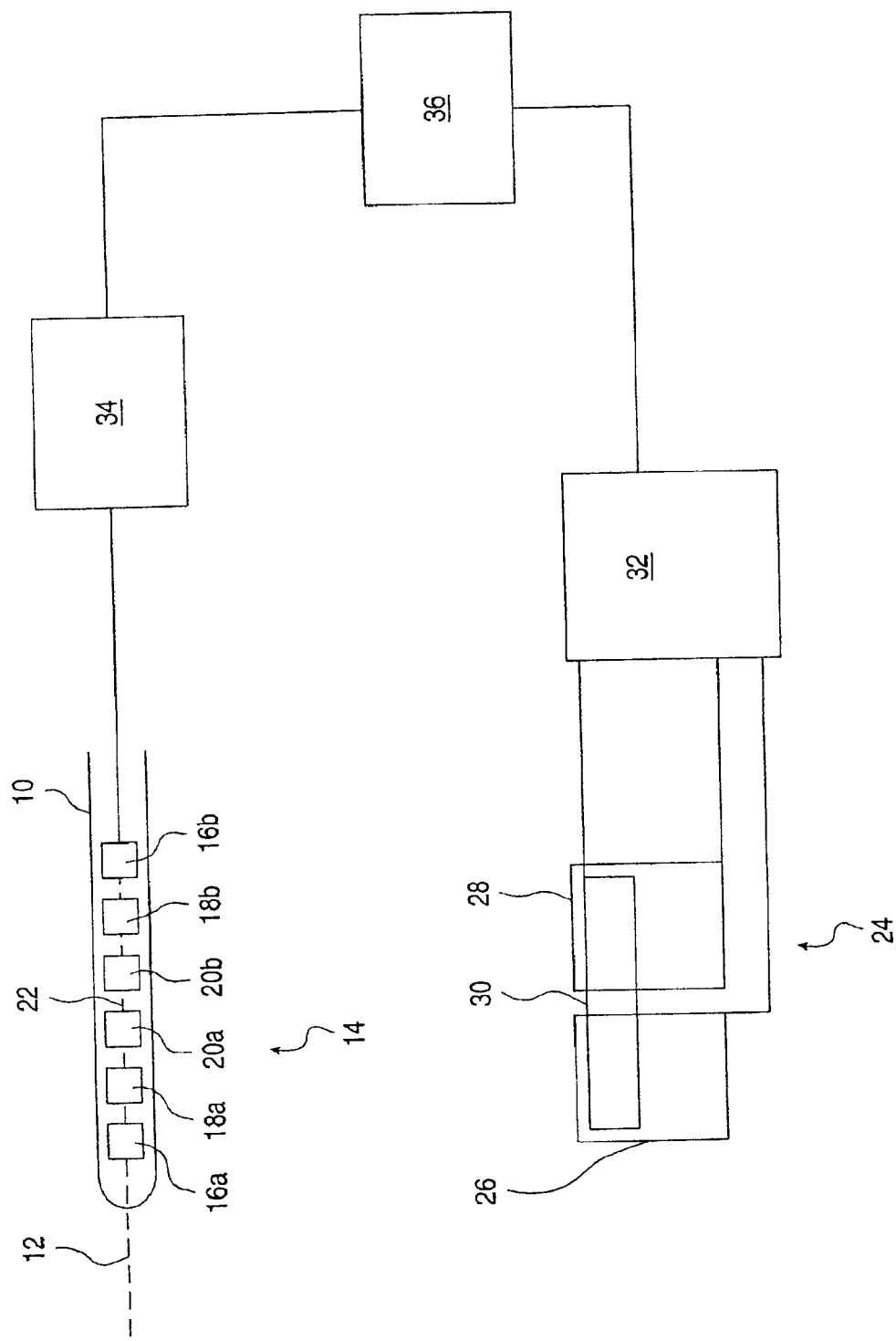
FIG. 1 is a schematic diagram of a system of the present invention.

Referring now to the drawings, FIG. 1 illustrates, in general terms, a system of the present invention. Within a probe 10 is rigidly mounted a receiver 14. Receiver 14 includes three field component sensors 16, 18, and 20, each for sensing a different component of an electromagnetic field. Sensor 16 includes two sensor elements 16a and 16b. Sensor 18 includes two sensor elements 18a and 18b. Sensor 20 includes two sensor elements 20a and 20b. Typically, the sensor elements are coils, and the sensed components are independent magnetic field components. Sensor elements 16a and 16b are on opposite sides of, and equidistant from, a common reference point 22. Similarly, sensor elements 18a and 18b are on opposite sides of, and equidistant from, point 22, and sensor elements 20a and 20b also are on opposite sides of, and equidistant from, point 22. In the illustrated example, sensors 16, 18 and 20 are disposed collinearly along a longitudinal axis 12 of probe 10, but other configurations are possible, as discussed below.

The system of FIG. 1 also includes a transmitter 24 of electromagnetic radiation. Transmitter 24 includes three substantially coplanar rectangular loop antennas 26, 28 and 30 connected to driving circuitry 32. Loop antennas 26 and 28 are adjacent and are partly overlapped by loop antenna 30. Driving circuitry 32 includes appropriate signal generators and amplifiers for driving each of loop antennas 26, 28 and 30 at a different frequency. The electromagnetic waves generated by transmitter 24 are received by receiver 14. The signals from receiver 14 that correspond to these electromagnetic waves are sent to reception circuitry 34 that includes appropriate amplifiers and A/D converters. Reception circuitry 34 and driving circuitry 32 are controlled by a controller/processor 36 that typically is an appropriately programmed personal computer. Controller/processor 36 directs the generation of transmitted signals by driving circuitry 32 and the reception of received signals by reception circuitry 34. Controller/processor 36 also implements the algorithm described below to infer the position and orientation of probe 10. Note that the system of FIG. 1 is a closed-loop system: the reception of signals from receiver 14 is synchronized with the transmission of electromagnetic waves by transmitter 24.

Figure 2A:
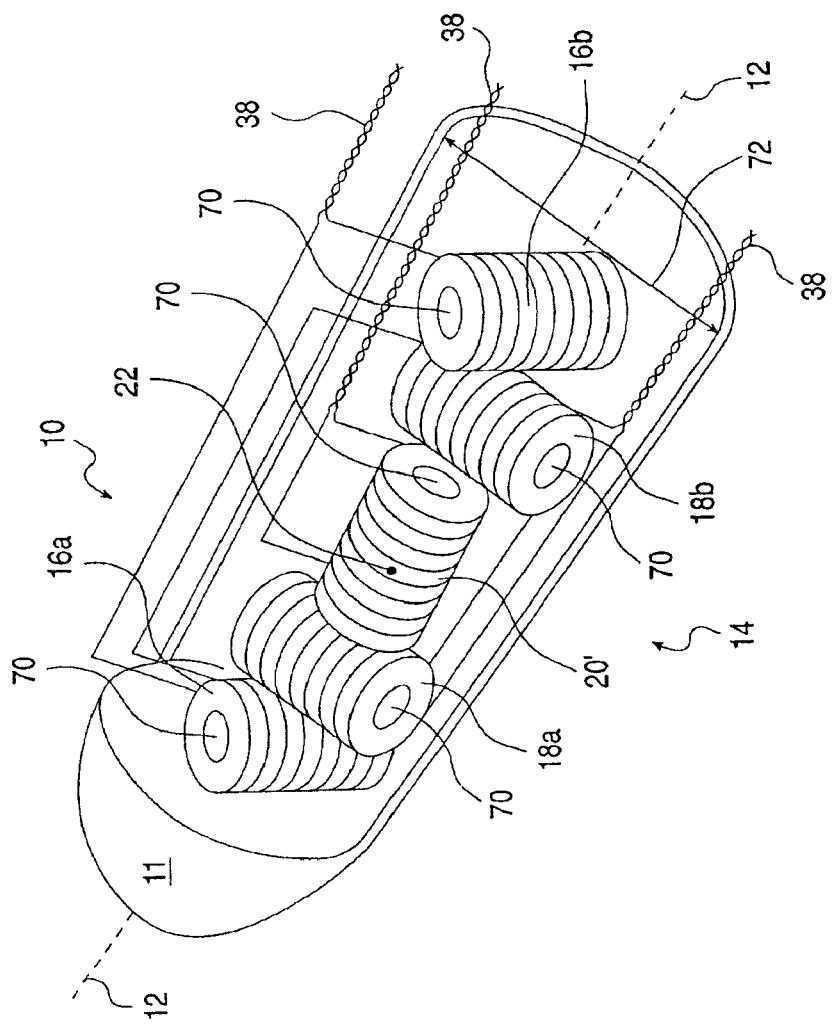
FIG. 2A is a partly cut away perspective view of a probe and a receiver.
Figure 2B:
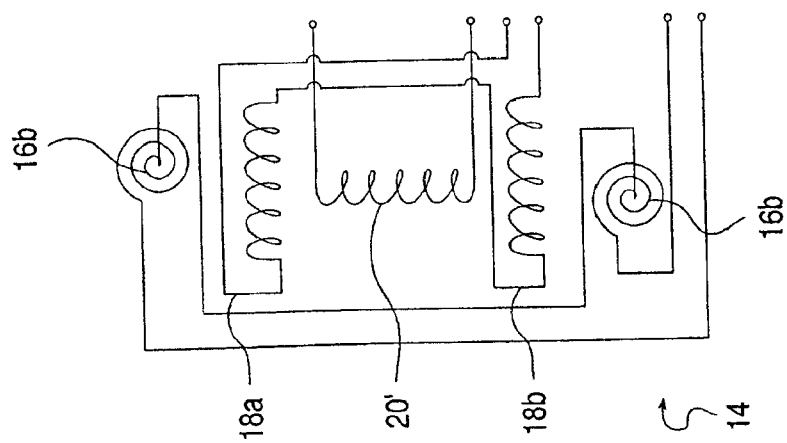
FIG. 2B is a circuit diagram of the receiver of FIG. 2A.

FIG. 2 shows a particular, slightly modified embodiment of receiver 14. FIG. 2A is a perspective, partly cut away view of probe 10 with receiver 14 mounted in the housing 11 thereof. FIG. 2B is a circuit diagram of receiver 14. In this embodiment, sensor elements 16a, 16b, 18a and 18b are coils of conducting wire wound on ferrite cores 70. Coils 16a and 16b are mutually parallel. Coils 18a and 18b are mutually parallel and are perpendicular to coils 16a and 16b. Coils 16a, 16b, 18a and 18b all are perpendicular to axis 12. Instead of sensor 20 with two sensor elements 20a and 20b, the embodiment of FIG. 2 has a single coil 20' of conducting wire wound on a ferrite core 70. Coil 20' is parallel to axis 12 and therefore is perpendicular to coils 16a, 16b, 18a and 18b. Coil 20' is centered on reference point 22. Sensors 16, 18 and 20' are connected to reception circuitry 34 by twisted wire pairs 38. As shown in the circuit diagram of FIG. 2B, coils 16a and 16b are connected in series, and coils 18a and 18b are connected in series.

Because sensors 16, 18 and 20' of FIG. 2 all measure field components at the same reference point 22, coils 16a, 16b, 18a, 18b and 20' can be wound on ferrite cores 70 instead of the air cores of WO 96/05768 without causing undue distortion of the received signals, despite the small transverse interior diameter 72, typically less than two millimeters, of probe 10 when probe 10 is a catheter.

Figure 2C:
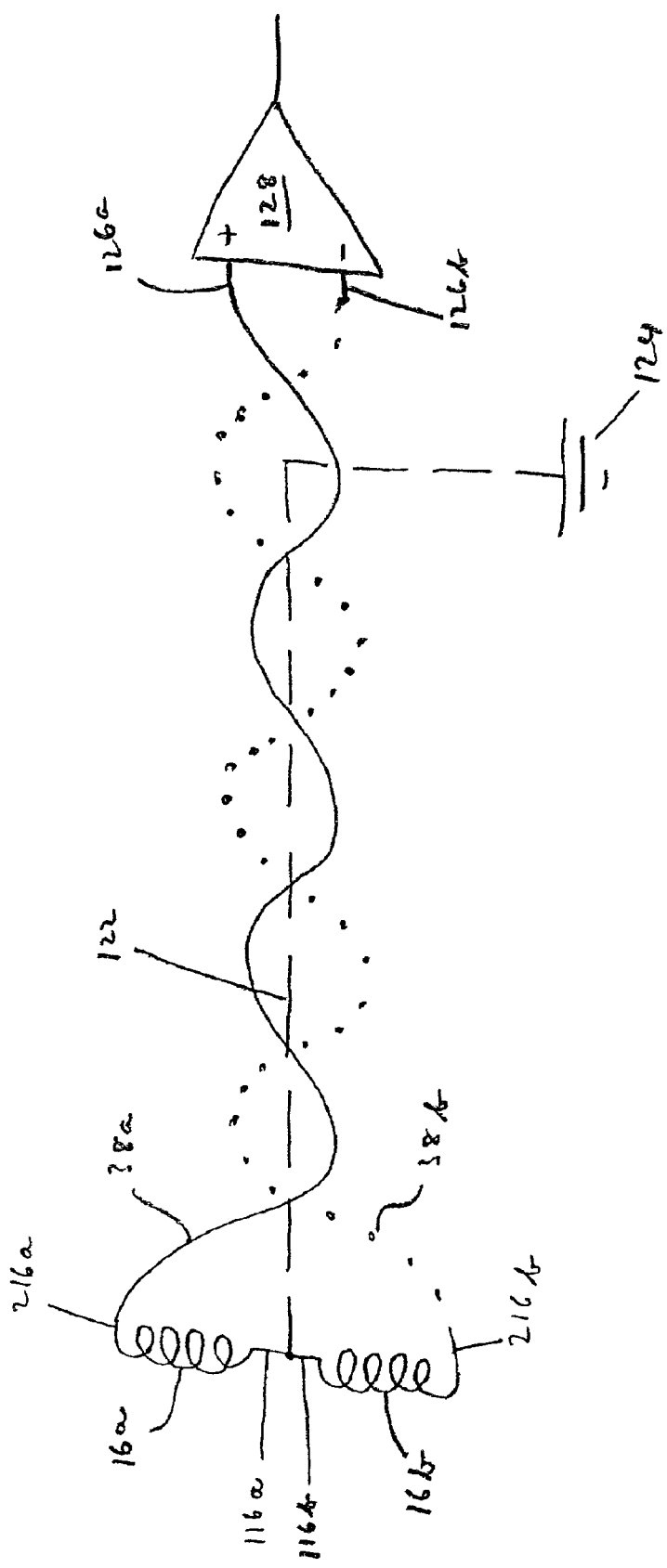
FIG. 2C illustrates features of the receiver of FIG. 2A that suppress unwanted electromagnetic coupling.

Wire pairs 38 are twisted in order to suppress electromagnetic coupling between wire pairs 38 and the environment, and in particular to suppress electromagnetic coupling between wire pairs 38 and transmitter 24. FIG. 2C is a circuit diagram that shows further features of the present invention that suppress this electromagnetic coupling. FIG. 2C is drawn with particular reference to sensor 16, but the same features apply, mutatis mutandis, to sensor 18.

Coils 16a and 16b are connected in series by inner leads 116a and 116b thereof. Outer lead 216a of coil 16a is connected, by wire 38a of twisted wire pair 38, to a positive input 126a of a differential amplifier 128 of reception circuitry 34. Outer lead 216b of coil 16b is connected, by wire 38b of twisted wire pair 38, to a negative input 126b of differential amplifier 128. Inner leads 116a and 116b also are connected to ground 124 by a wire 122. For illustrational clarity, wire 38a is drawn as a solid line, wire 38b is drawn as a dotted line and wire 122 is drawn as a dashed line.

Figure 15:
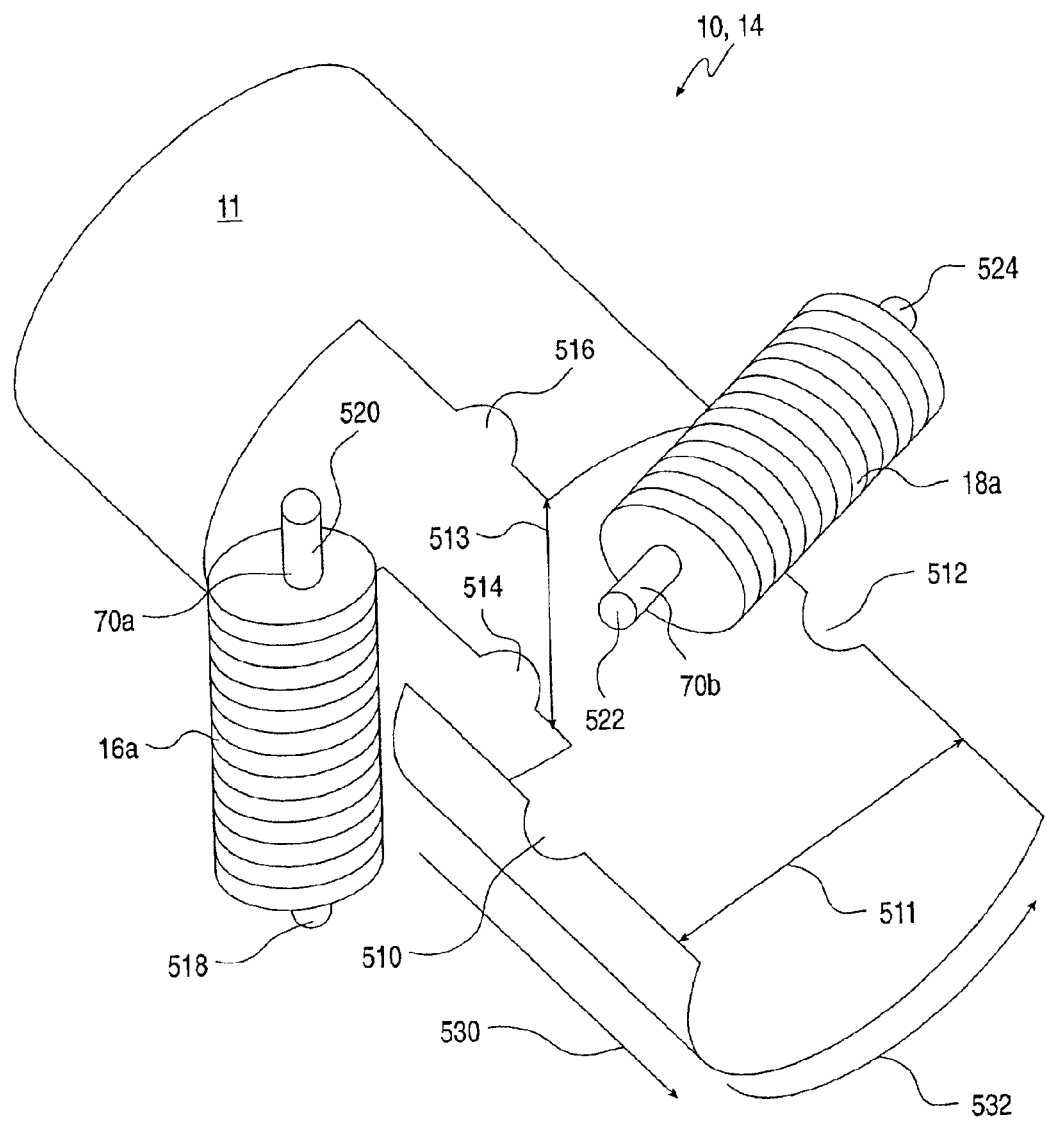
FIG. 15 is a partial exploded perspective view of a preferred embodiment of the probe and receiver of FIG. 2A.

FIG. 15 is a partial exploded perspective view of a preferred embodiment of probe 10 and receiver 14. Housing 11 is substantially cylindrical, with two recesses 511 and 513 incised therein. The boundary of each recess 511 or 513 includes a pair of diametrically opposed apertures: apertures 510 and 512 in the boundary of recess 511 and apertures 514 and 516 in the boundary of recess 513. Arrows 530 and 532 show two of the three components of a cylindrical coordinate system for describing position within and along housing 11. Arrow 530 points in the longitudinal direction. Arrow 532 points in the azimuthal direction. Aperture pair 510, 512 is displaced both longitudinally and azimuthally from aperture pair 514, 516.

Coil 16a is a coil of electrically conducting wire that is wound about a core 70a. Core 70a is mounted in apertures 514 and 516: end 518 of core 70a, that extends beyond coil 16a, is mounted in aperture 514 and is secured rigidly in place by a suitable glue, and end 520 of core 70a, that extends beyond coil 16a in the opposite direction, is mounted in aperture 516 and is secured rigidly in place by a suitable glue. Similarly, coil 18a is a coil of electrically conducting wire that is wound about a core 70b. Core 70b is mounted in apertures 510 and 512: end 522 of core 70b, that extends beyond coil 18a, is mounted in aperture 510 and is secured rigidly in place by a suitable glue, and end 524 of core 70b, that extends beyond coil 18a in the opposite direction, is mounted in aperture 512 and is secured rigidly in place by a suitable glue.

FIG. 15 also shows the preferred azimuthal separation of aperture pair 514, 516 from aperture pair 510, 512. Aperture pair 514, 516 is perpendicular to aperture pair 510, 512, in the sense that aperture pair 514, 516 is displaced 90°, in the direction of arrow 532, from aperture pair 510, 512. This makes core 70a perpendicular to core 70b, and hence makes coils 16a and 18a mutually perpendicular.

In the case of probe 10 being a catheter for invasively probing or treating a body cavity such as a chamber of the heart, it is preferable that housing 11 be made of a nonmagnetic metal such as nitinol, titanium, iconel, phynox or stainless steel. Housing 11 thus is sufficiently flexible to bend under the lateral forces of the walls of blood vessels through which probe 10 is inserted towards the body cavity, and sufficiently resilient to return to its unstressed shape, with coils 16a and 18a mutually perpendicular, when the portion of probe 10 that includes receiver 14 reaches the interior of the body cavity. Surprisingly, it has been found that the use of a conductive metal as the material of housing 11 does not distort the electromagnetic field sensed by receiver 14 despite the current eddies induced in housing 11 by the electromagnetic waves generated by transmitter 24. Apertures 510, 512, 514 and 516 are most conveniently formed by laser cutting. The accuracy of the mutual perpendicularity of coils 16a and 18a obtained in this manner has been found to be superior to the accuracy obtained by forming housing 11 as a solid cylindrical block and drilling mutually perpendicular recesses in the block to receive coils 16a and 18a.

Coils 16b and 18b are mounted similarly in similar pairs of diametrically opposed, azimuthally and longitudinally displaced apertures. This ensures that coils 16a and 16b are mutually parallel, that coils 18a and 18b are mutually parallel, and that coils 16b and 18b are mutually perpendicular.

In an alternative structure (not shown) of housing 11, housing 11 is formed as an open, spring-like frame that includes apertures 510, 512, 514 and 516 in the form of small rings that are sized to accept the ends 518, 520, 522 and 524 of cores 70a and 70b. The spring-like nature of this embodiment of housing 11 allows coils 16a and 18a to be mounted therein simply by forcing ends 518, 520, 522 and 524 into their respective apertures, and also allows housing 11 to flex during insertion towards a body cavity of a patient and to return to its unstressed shape upon arrival inside the body cavity.

Figure 3:
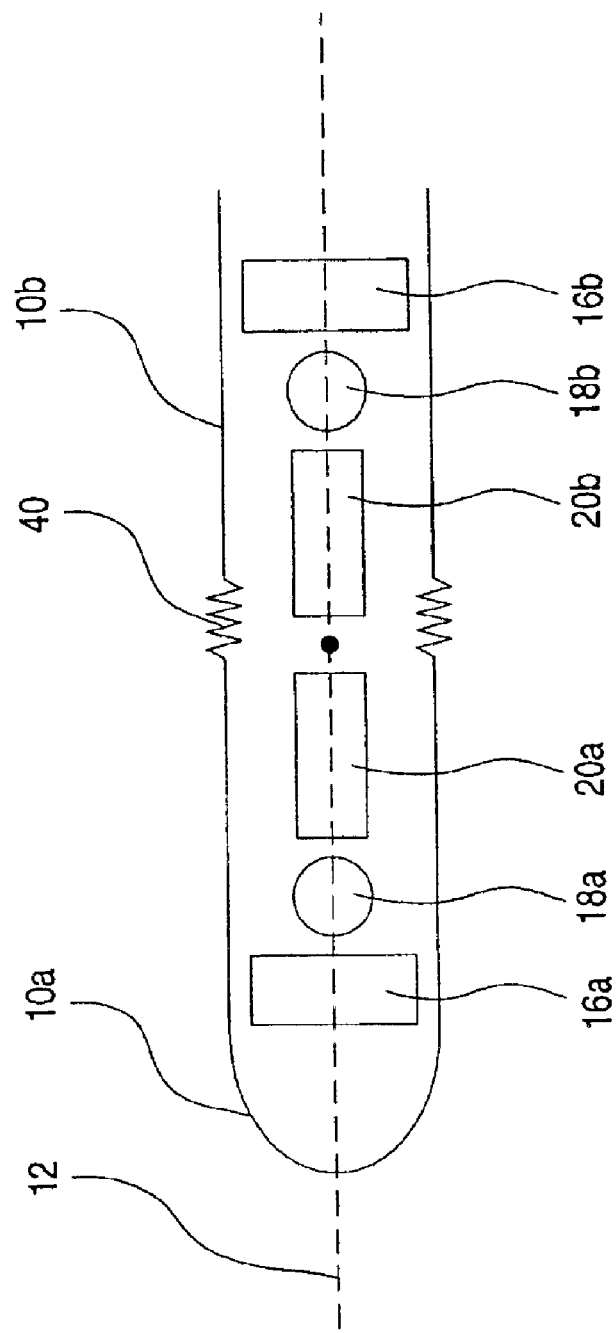
FIG. 3 is an axial sectional view of a probe and a receiver.

FIG. 3 is an axial sectional view of receiver 14 mounted in a variant of probe 10 that has two sections 10a and 10b connected by a flexible connector 40. As in FIG. 2, sensors 16 and 18 include sensor elements 16a, 16b, 18a and 18b that are coils of conducting wire wound on air cores and that are perpendicular to axis 12. Sensor elements 16a and 16b are mutually parallel, sensor elements 18a and 18b are mutually parallel, and sensor elements 16a and 16b are perpendicular to sensor elements 18a and 18b. Sensor 20 includes two sensor elements: coils 20a and 20b of conducting wire wound on air cores. Coils 20a and 20b are equidistant from reference point 22 and are parallel to axis 12. Like coils 16a and 16b and like coils 18a and 18b, coils 20a and 20b are connected in series. Flexible connector 40 allows this variant of probe 10 to bend as this variant of probe 10 is moved within a medical patient. Sensor element pairs 16, 18 and 20 are disposed symmetrically with respect to reference point 22 in the sense that when probe 10 of FIG. 3 is straight, as drawn, sensor elements 16a and 16b are on opposite sides of, and equidistant from, reference point 22; and likewise sensor elements 18a and 18b are on opposite sides of, and are equidistant from, reference point 22; and sensor elements 20a and 20b are on opposite sides of, and are equidistant from, reference point 22. Note that when probe 10 of FIG. 3 is straight, sensor elements 16a, 16b, 18a, 18b, 20a and 20b all are collinear, along axis 12 that intersects point 22, and so are disposed symmetrically with respect to point 22.

Figure 4A:
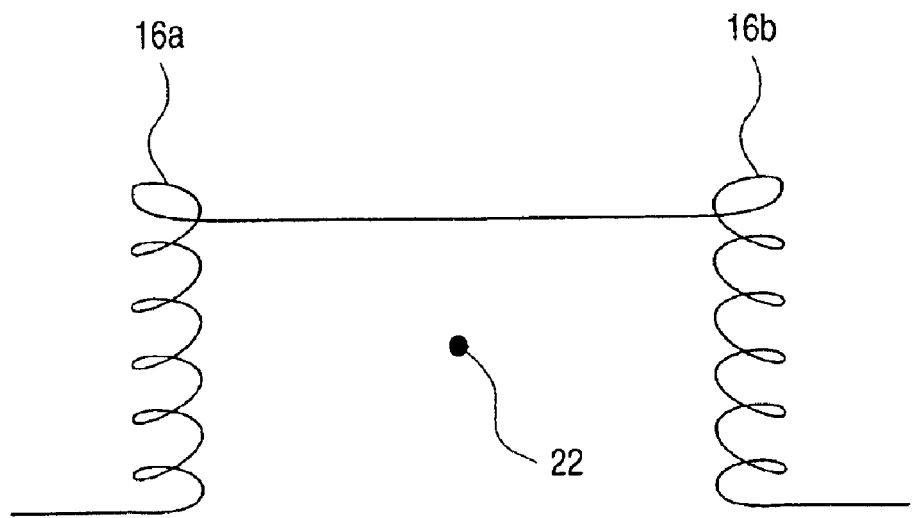
FIG. 4A shows two coils of opposite helicities.
Figure 4B:
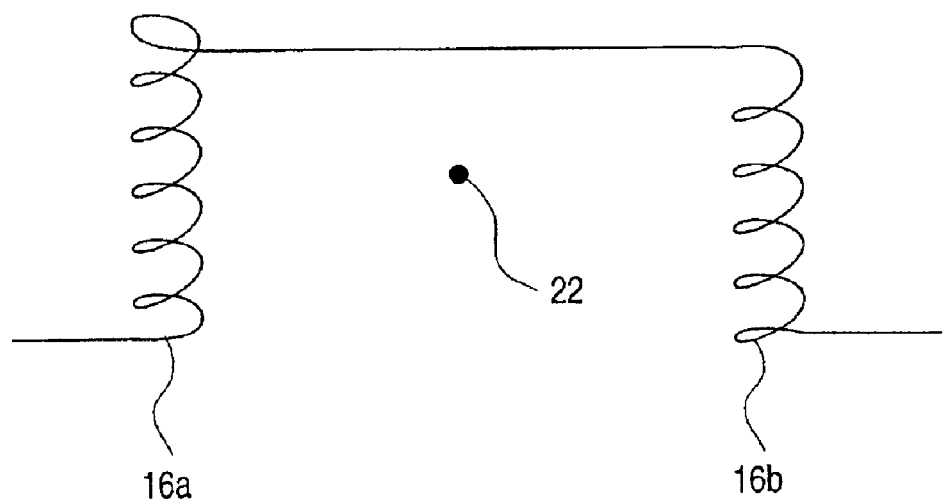
FIG. 4B shows two coils of identical helicities.

For coil pairs such as pairs 16a and 16b to produce signals representative of a magnetic field component at point 22 when the coil pairs are connected as shown in FIG. 2A, the two coils must have opposite helicity, as illustrated in FIG. 4A, so that, in a spatially uniform time varying magnetic field, the signals induced in the two coil pairs 16a and 16b reinforce each other instead of canceling each other. Coil pairs 16a and 16b that have identical helicities, as illustrated in FIG. 4B, may be used to measure a magnetic field component gradient at point 22. Alternatively, coil pairs of identical helicities may be used to measure magnetic field components if the top of one coil is connected to the bottom of the other coil.

Figure 5:
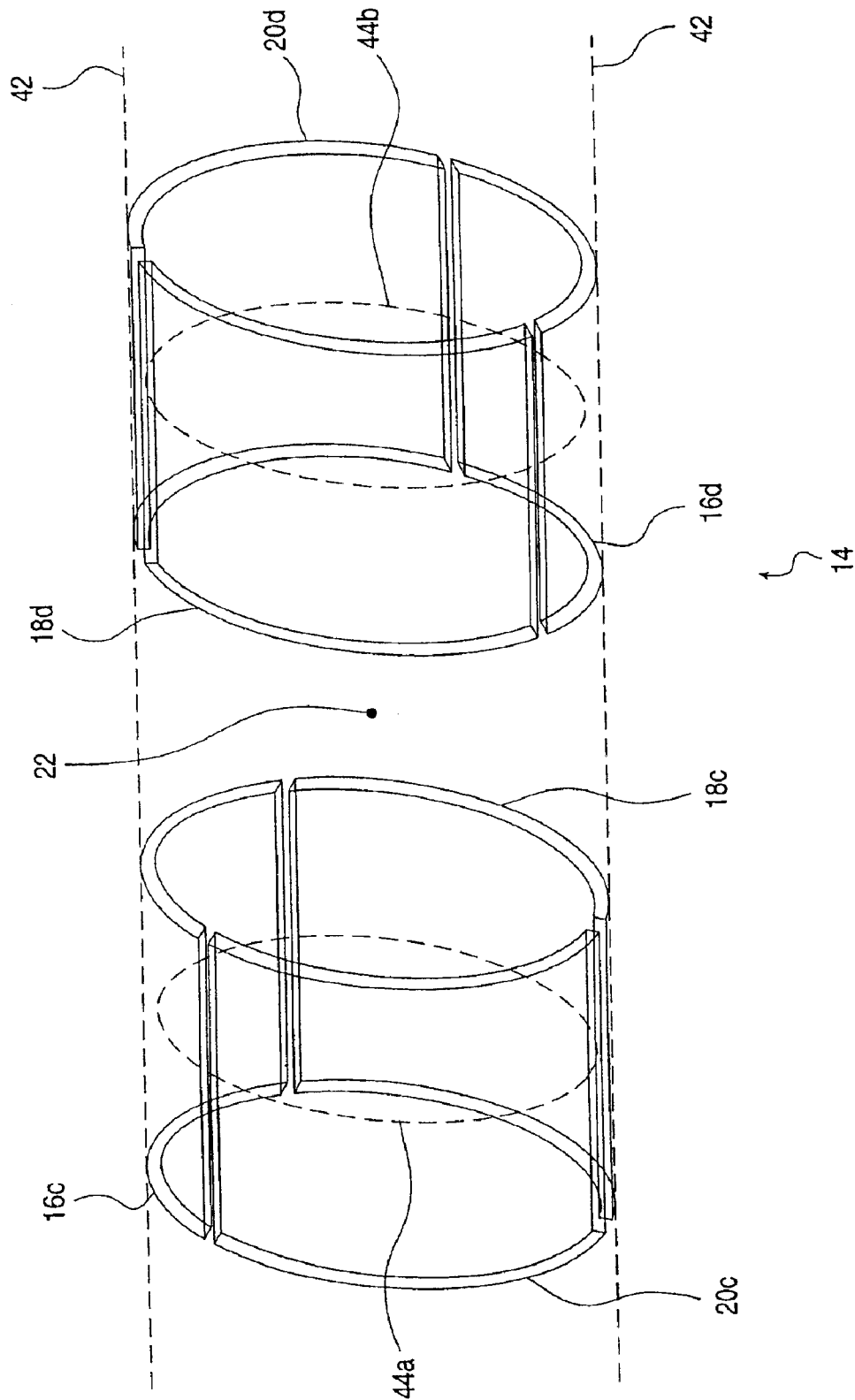
FIG. 5 shows a second preferred embodiment of a receiver.
Figure 10:
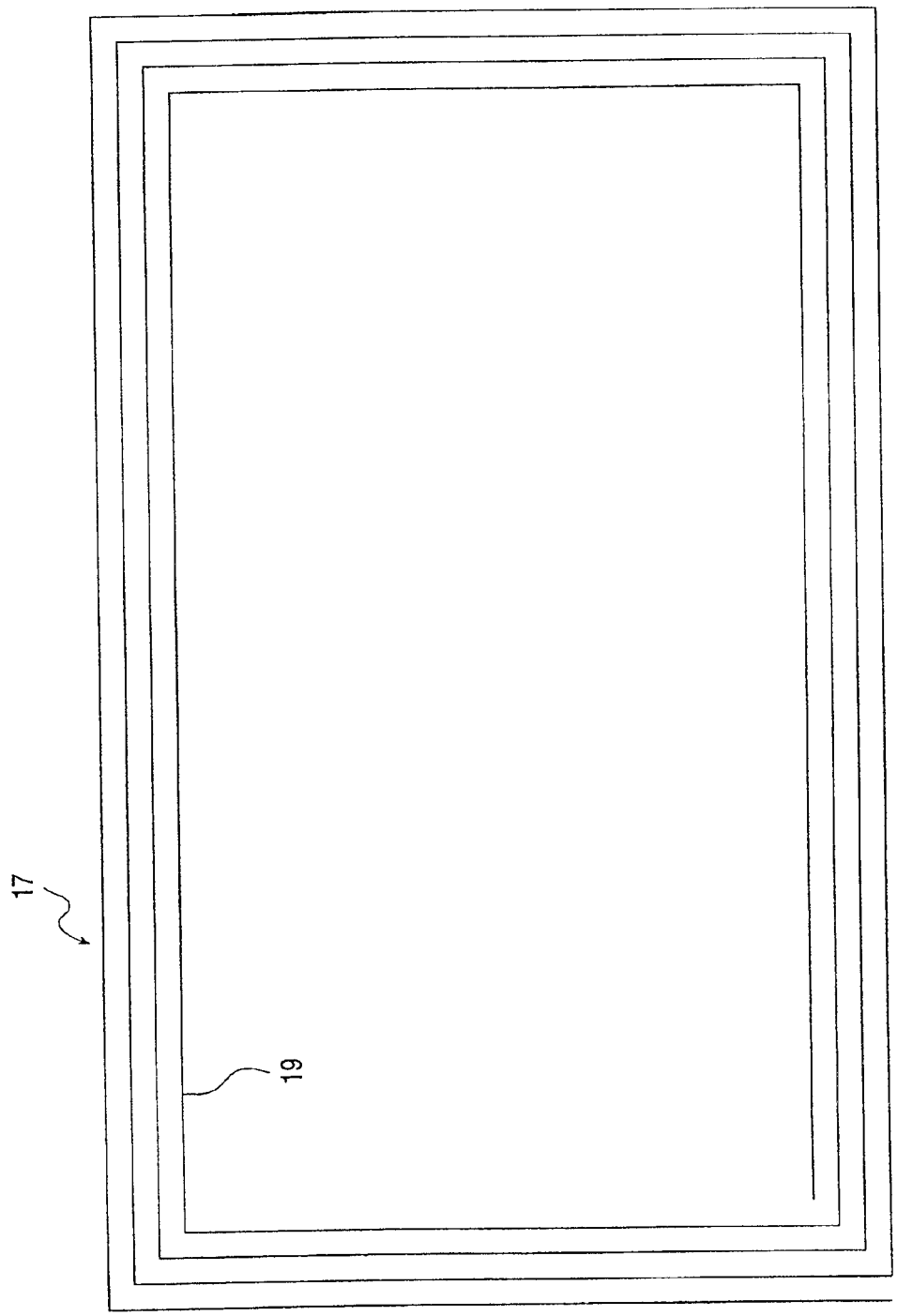
FIG. 10 shows a coil of the receiver of FIG. 5.

FIG. 5 illustrates a second class of preferred embodiments of receiver 14. In FIG. 5, a conceptual cylindrical surface is denoted by dashed lines 42 and dashed circles 44. The embodiment of receiver 14 illustrated in FIG. 5 includes three sensors 16, 18 and 20, each with two sensor elements 16c and 16d, 18c and 18d, and 20c and 20d, respectively. Each sensor element is a flat rectangular coil, of many turns of conducting wire, that is bent into an arcuate shape to conform to the shape of the cylindrical surface. Sensor elements 16c, 18c and 20c are interleaved around circle 44a. Sensor elements 16d, 18d and 20d are interleaved around circle 44b. Sensor elements 16c and 16d are disposed symmetrically with respect to reference point 22, meaning that sensor elements 16c and 16d are on opposite sides of reference point 22, are equidistant from reference point 22, and are oriented so that an appropriate 180° rotation about point 22 maps sensor 16c into sensor 16d. Similarly, sensor elements 18c and 18d are disposed symmetrically with respect to reference point 22, and sensor elements 20c and 20d are disposed symmetrically with respect to reference point 22. Sensor elements 16c and 16d are connected in series, in a manner similar to sensor elements 16a and 16b, to respond to one component of the magnetic field. Sensor elements 18c and 18d are connected similarly in series to respond to a second component of the magnetic field that is independent of the first component, and sensor elements 20c and 20d are connected similarly in series to respond to a third component of the magnetic field that is independent of the first two components. Most preferably, sensor elements 16c, 16d, 18c, 18d, 20c and 20d are sized and separated so that these three magnetic field components are orthogonal. In practice, the cylindrical surface whereabout sensor elements 16c, 16d, 18c, 18d, 20c and 20d are disposed could be the inner surface of probe 10 or the outer surface of a cylindrical sleeve adapted to fit inside probe 10. In the case of this embodiment of receiver 14 formed on the outer surface of a cylindrical sleeve, sensor elements 16c, 16d, 18c, 18d, 20c and 20d may be fabricated by any one of several standard methods, including photolithography and laser trimming. FIG. 10 illustrates the preferred geometry of sensor elements 16c, 16d, 18c, 18d, 20c and 20d: a flat rectangular spiral 17 of an electrical conductor 19. Only four turns are shown in spiral 17, for illustrational simplicity. Preferably, however, there are several hundred turns in spiral 17. For example, a spiral 17, intended for a cylindrical surface of a diameter of 1.6 millimeters, in which conductor 19 has a width of 0.25 microns, and in which the windings are separated by gaps of 0.25 microns, has 167 turns.

Figure 12A:
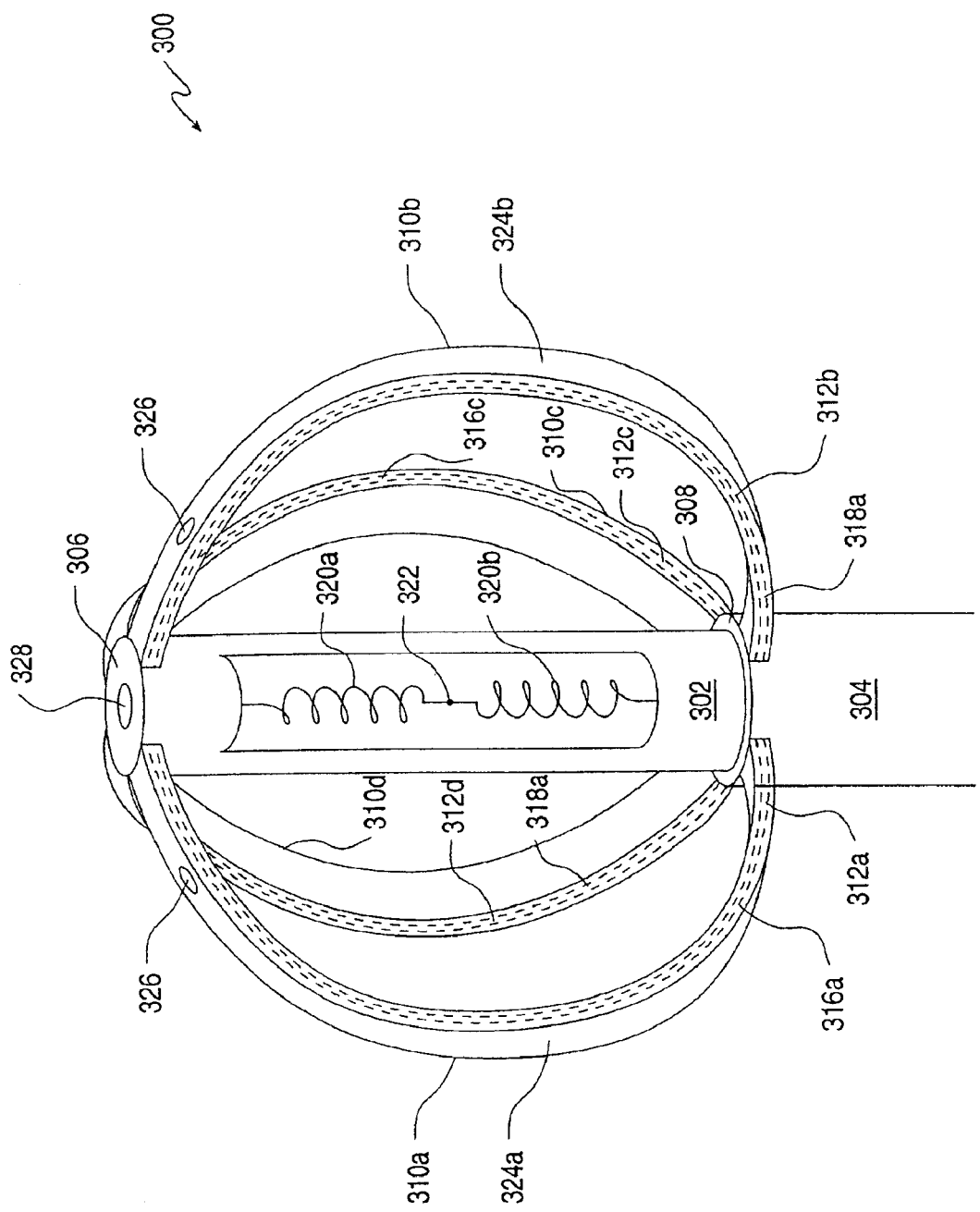
FIG. 12A is a partly cut-away perspective view of a cardiac catheter of the present invention in the retracted position thereof.
Figure 12B:
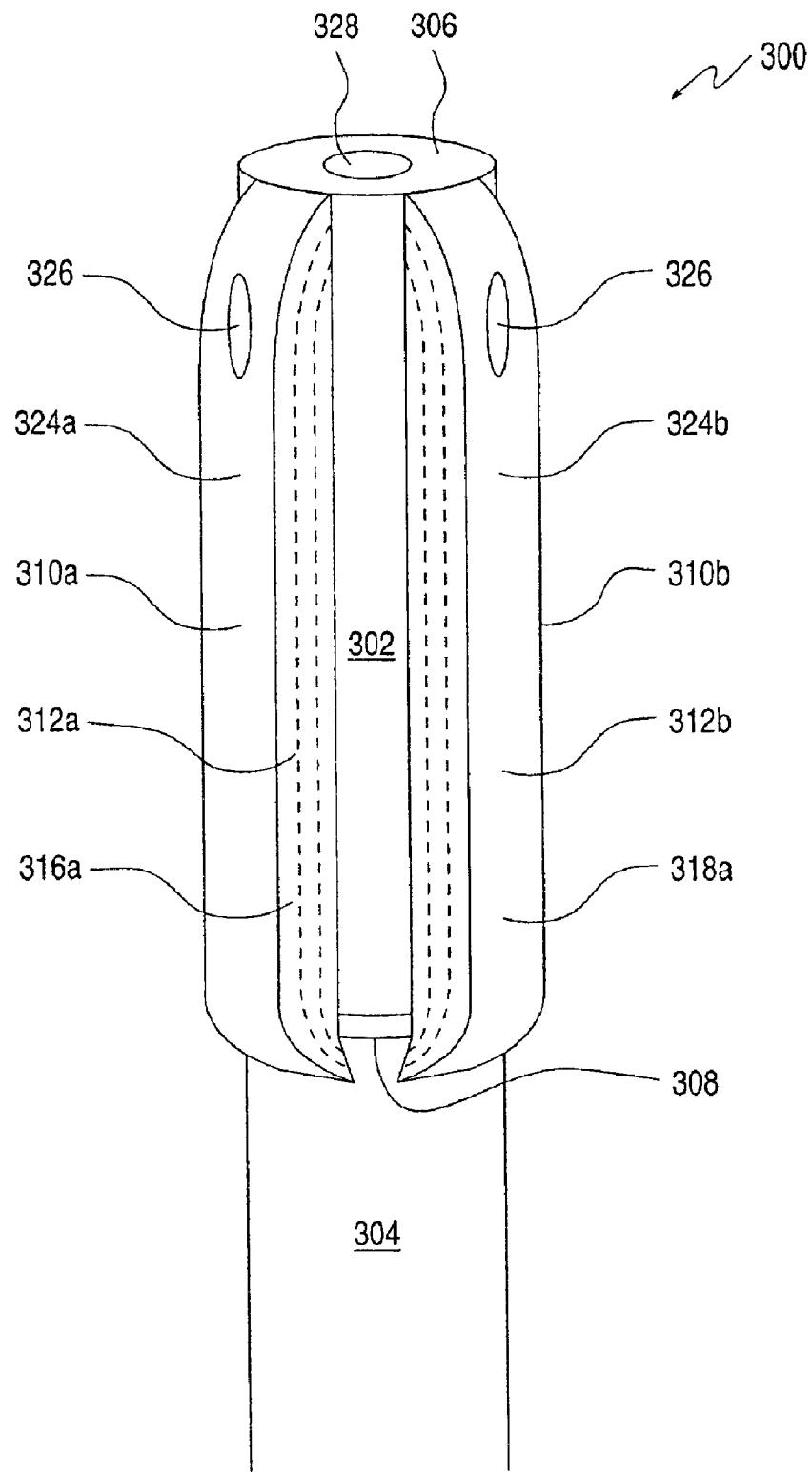
FIG. 12B is a perspective view of the catheter of FIG. 12A in the extended position thereof.
Figure 12C:
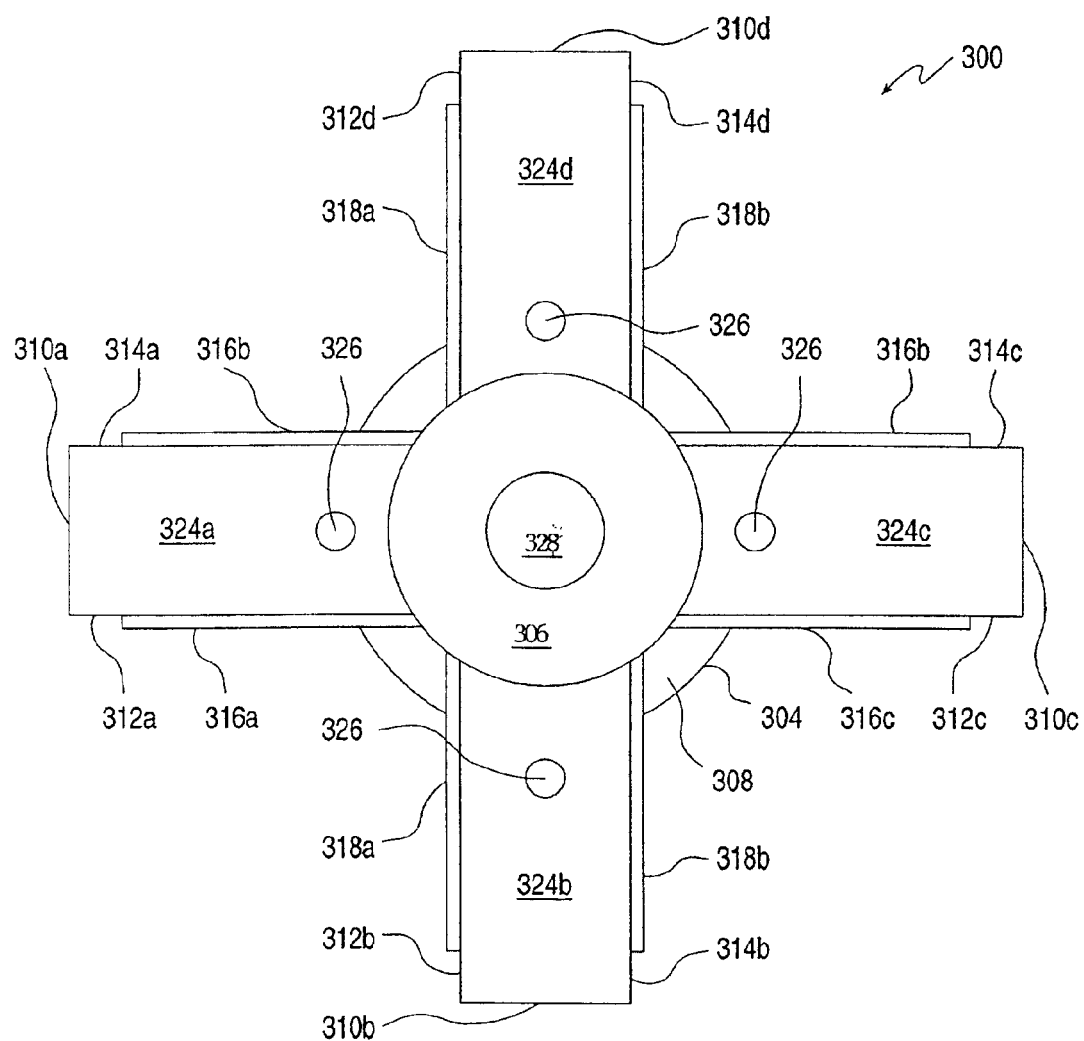
FIG. 12C is an end-on view of the catheter of FIG. 12a in the retracted position thereof.

FIGS. 12A, 12B and 12C illustrate the distal end of a cardiac catheter 300 of the present invention. FIG. 12A is a partly cut-away perspective view of catheter 300 in the retracted position thereof. FIG. 12B is a perspective view of catheter 300 in the extended position thereof. FIG. 12C is an end-on view of catheter 300 in the retracted position thereof. Catheter 300 includes a flexible cylindrical inner sleeve 302 slidably mounted in a flexible cylindrical outer sleeve 304. Connecting distal end 306 of inner sleeve 302 to distal end 308 of outer sleeve 304 are four flexible rectangular strips 310. When inner sleeve 302 is in the extended position thereof relative to outer sleeve 304, strips 310 are flush against inner sleeve 302, as shown in FIG. 12B. When inner sleeve 302 is in the retracted position thereof relative to outer sleeve 304, strips 310 bow outward in circular arcs, as shown in FIG. 12A.

Catheter 300 includes a set of three orthogonal electromagnetic field component sensors 316, 318 and 320, in the manner of receiver 14 of FIG. 1. First sensor 316 includes coils 316a and 316b mounted on opposite lateral edges 312a and 314a of strip 310a and on opposite lateral edges 312c and 314c of strip 310c. Coil 316a is mounted on lateral edges 312a and 312c. Coil 316b is mounted on lateral edges 314a and 314b. Second sensor 318 includes coils 318a and 318b mounted on opposite lateral edges 312b and 314b of strip 310b and on opposite lateral edges 312d and 314d of strip 310d. Coil 318a is mounted on lateral edges 312b and 312d. Coil 318b is mounted on lateral edges 314b and 314d. Third sensor 320 includes coils 320a and 320b. Inner sleeve 302 is cut away in FIG. 12A to show coils 320a and 320b. For illustrational clarity, the wires of coils 316a and 318a are shown in FIGS. 12A and 12B as dashed lines, and only two turns are shown for each coil, although in practice at least nine turns of 45-micron-diameter copper wire are used. Note that the wires of coil 316a run through inner sleeve 302, from lateral edge 312a to lateral edge 312c, and do not terminate at the intersection of lateral edges 312a and 312c with inner sleeve 302. Similarly, the wires of coil 318a do not terminate at the intersection of lateral edges 312b and 312d with inner sleeve 302, but instead run from lateral edge 312b to lateral edge 312d. Also for illustrational clarity, lateral edges 312 are shown much wider than they really are in preferred embodiments of catheter 300. Coils 320a and 320b are wound around a permeable core (not shown).

In a typical embodiment of catheter 300, the length of inner sleeve 302 exceeds the length of outer sleeve 304 by 15.7 mm in the extended position. Also in a typical embodiment of catheter 300, each of coils 320a and 320b is about 1.1 mm long and about 1.1 mm in diameter and includes about 400 turns of 10 micron diameter copper wire.

Coils 320a and 320b are parallel and equidistant from a central point 322. When catheter 300 is opened to the retracted position thereof, as shown in FIGS. 12A and 12C, the circular arcs formed by strips 310 are concentric with point 322. This makes coils 316a, 316b, 318a and 318b circular and concentric with point 322, with coils 316a and 316b being mutually parallel, and with coils 318a and 318b being mutually parallel, so that point 322 then becomes the reference point for electromagnetic field measurements.

In the extended position thereof, catheter 300 is thin enough, preferably less than about 2 mm in diameter, to be inserted via the blood vessels of a patient into the patient's heart. Once the distal end of catheter 300 is inside the desired chamber of the patient's heart, inner sleeve 302 is withdrawn relative to outer sleeve 304 to put catheter 300 in the retracted position thereof. Sensors 316, 318 and 320 are used in conjunction with transmitter 24 in the manner described below to determine the location and orientation of the distal end of catheter 300 within the patient's heart.

Mounted on outward faces 324 of strips 310 are four electrodes 326. Mounted on distal end 306 of inner sleeve 302 is an electrode 328. Electrodes 326 and 328 may be used for electrophysiologic mapping of the patient's heart. Alternatively, high RF power levels may be applied to selected heart tissue via electrode 328 to ablate that tissue in the treatment of conditions such as ventricular tachycardia.

Figure 13A:
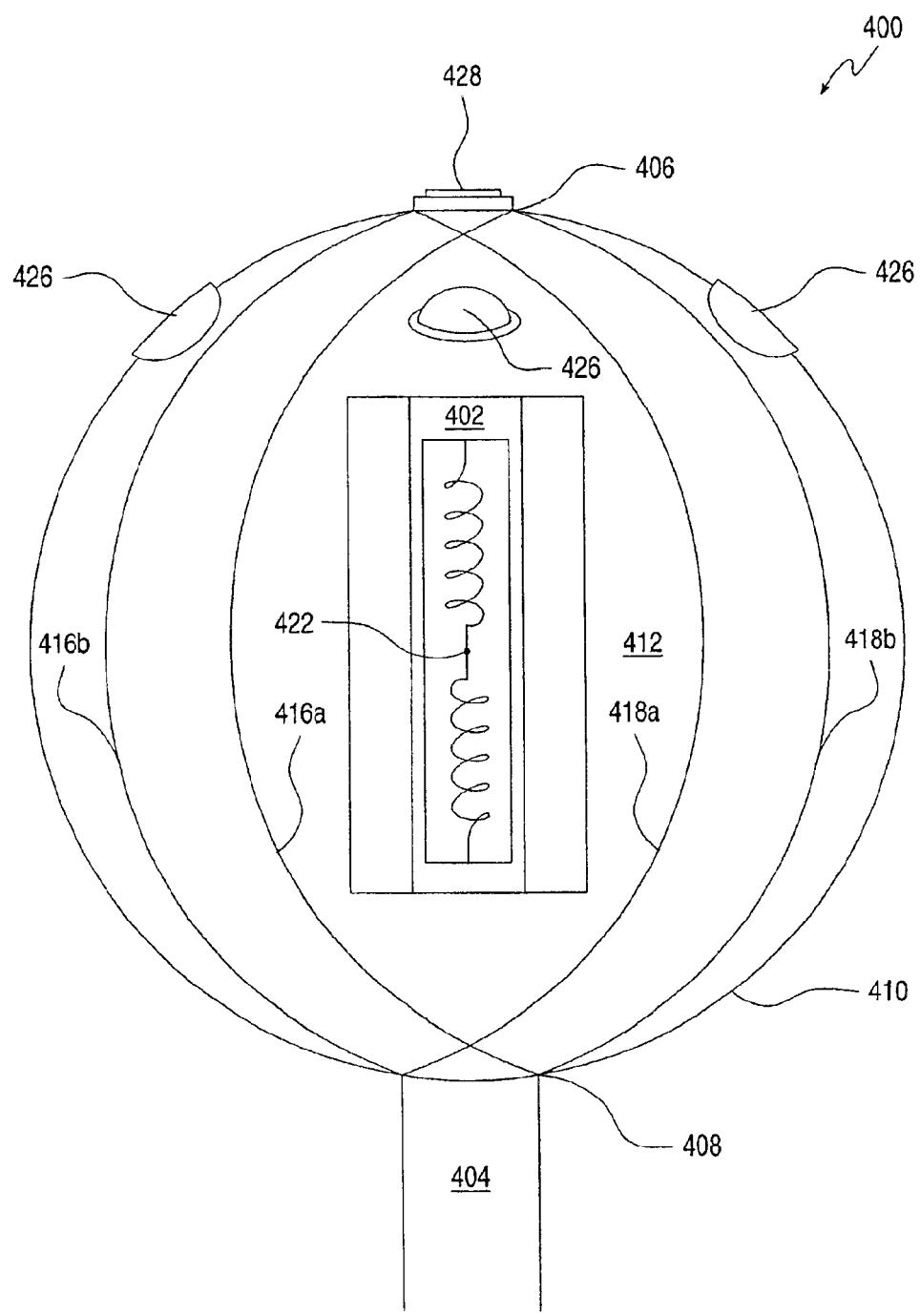
FIG. 13A is a partly cut-away side view of a second embodiment of the cardiac catheter of the present invention in the retracted and inflated position thereof.
Figure 13B:
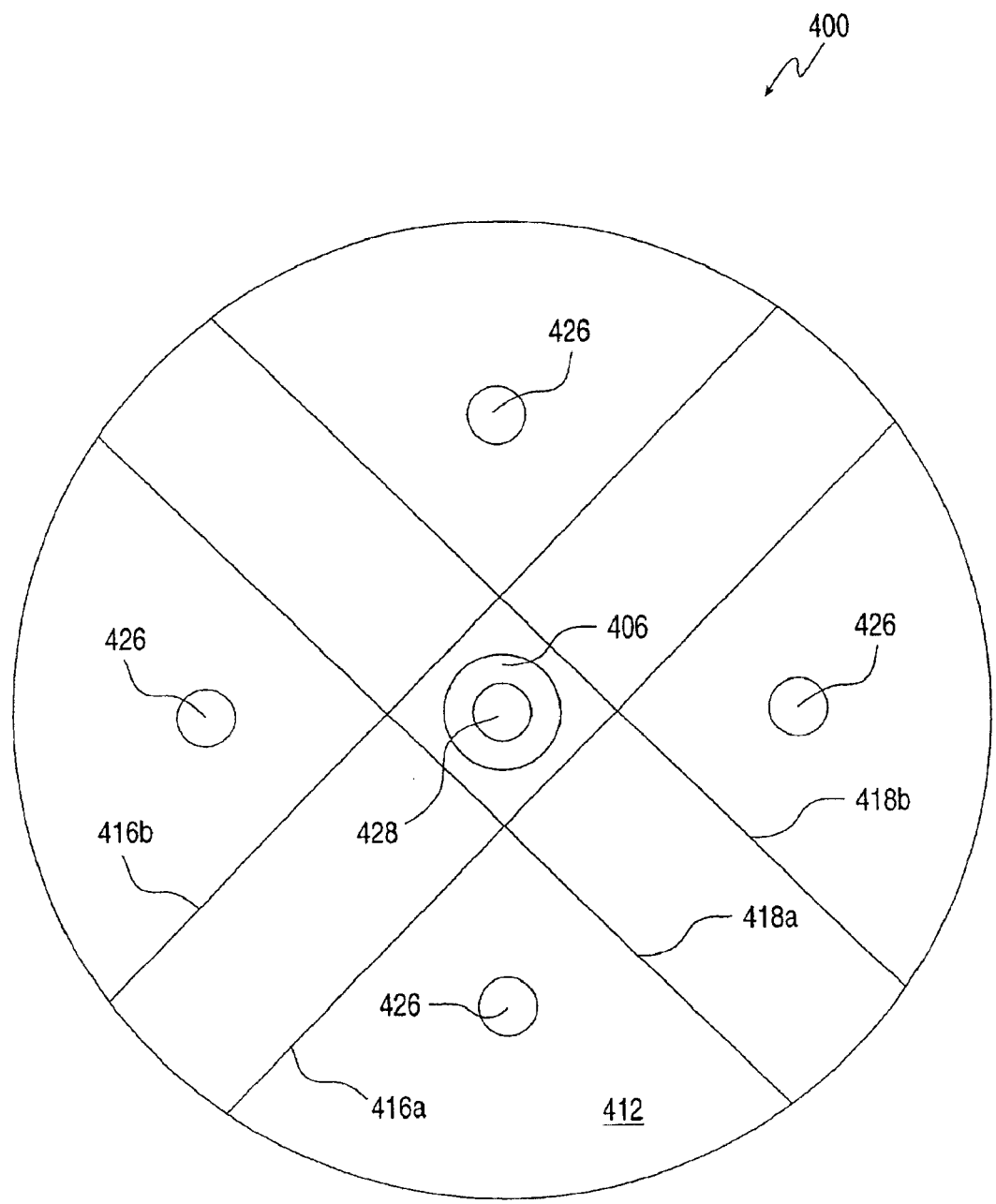
FIG. 13B is an end-on view of the catheter of FIG. 13A in the retracted and inflated position thereof.

FIGS. 13A and 13B illustrate the distal end of an alternative embodiment 400 of the cardiac catheter of the present invention. FIG. 13A is a partly cut-away side view of catheter 400 in the retracted position thereof. FIG. 13B is an end-on view of catheter 400 in the retracted position thereof. Like catheter 300, catheter 400 includes a flexible cylindrical inner sleeve 402 slidably mounted in a flexible cylindrical outer sleeve 404. Connecting distal end 406 of inner sleeve 402 to distal end 408 of outer sleeve 404 is a single flexible member: an inflatable latex balloon 410. When inner sleeve 402 is in the extended position thereof relative to outer sleeve 404, balloon 410 is flush against inner sleeve 402. After the illustrated distal end of catheter 400 has been introduced to the targeted chamber of a patient's heart, inner sleeve 402 is withdrawn to the retracted position thereof, and balloon 410 is inflated to assume a spherical shape.

Like catheter 300, catheter 400 includes a set of three orthogonal electromagnetic field component sensors 416, 418 and 420, in the manner of receiver 14 of FIG. 1. First sensor 416 includes parallel coils 416a and 416b mounted as shown on outer surface 412 of balloon 410. Second sensor 418 includes parallel coils 418a and 418b mounted orthogonally to coils 416a and 416b on outer surface 412, as shown. Third sensor 420 includes coils 420a and 420b. Balloon 410 and inner sleeve 402 are cut away in FIG. 13A to show coils 420a and 420b. Coils 420a and 420b are parallel and equidistant from a central point 422. When catheter 400 is opened to the retracted position thereof and balloon 410 is inflated to a spherical shape, outer surface 412 is a sphere concentric with point 422. This makes coils 416a, 416b, 418a and 418b circular and concentric with point 422, so that point 422 then becomes the reference point for electromagnetic field measurements.

Also as in the case of catheter 300, catheter 400 includes four electrodes 426, similar to electrodes 326, mounted on outer surface 412, and an electrode 428, similar to electrode 328, mounted on distal end 406 of inner sleeve 402.

Figure 6:
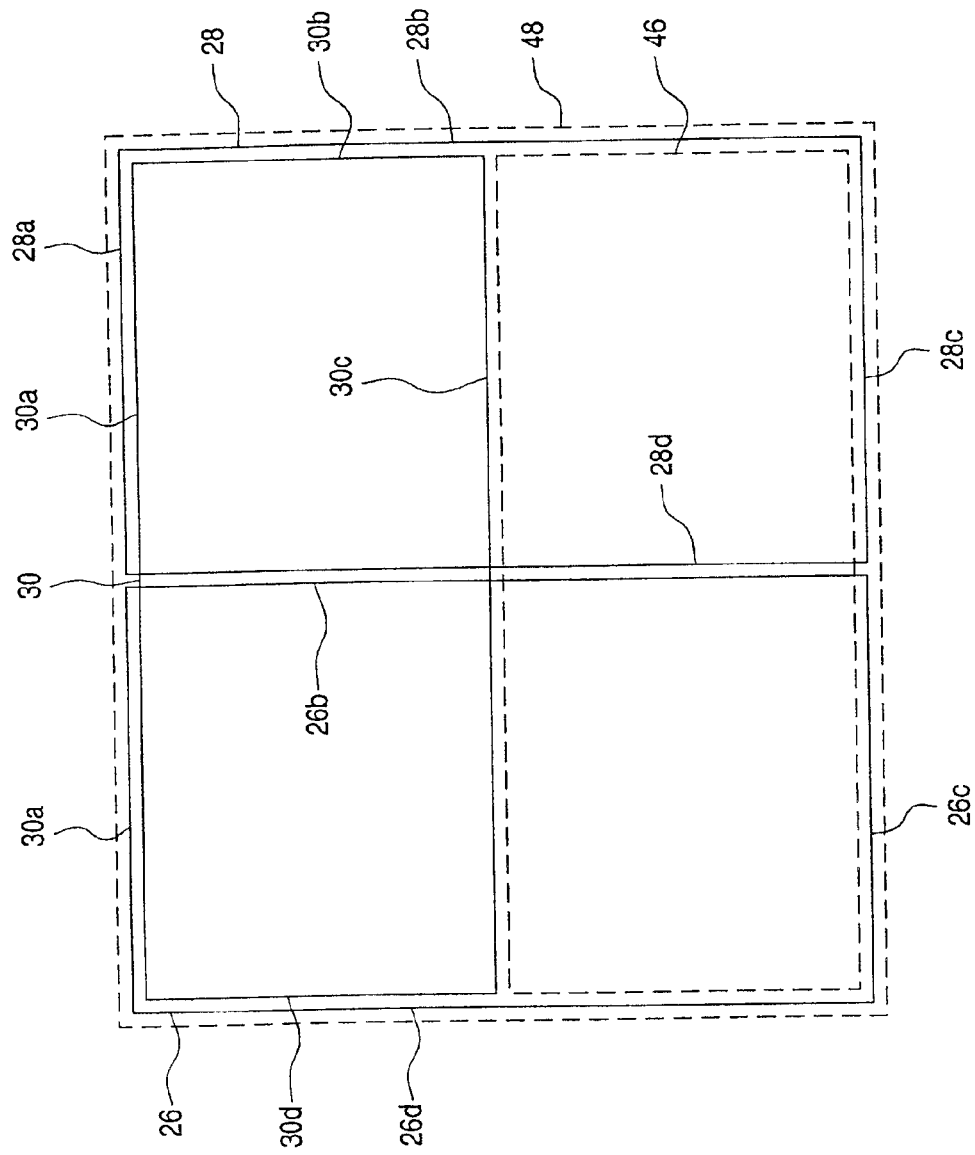
FIG. 6 is a plan view of three loop antennas and two phantom loop antennas.

FIG. 6 is a plan view of loop antennas 26, 28 and 30. Loop antenna 26 is a rectangle with legs 26a, 26b, 26c and 26d. Loop antenna 28 is a rectangle of the same shape and size as loop antenna 26, and with legs 28a, 28b, 28c and 28d. Legs 26b and 28d are adjacent. Loop antenna 30 also is rectangular, with legs 30a, 30b, 30c and 30d. Leg 30a overlies legs 26a and 28a; leg 30b overlies the upper half of leg 28b; and leg 30d overlies the upper half of leg 26d, so that loop antenna 30 overlaps half of loop antenna 26 and half of loop antenna 28. Also shown in phantom in FIG. 6 is a fourth rectangular loop antenna 46 and a fifth rectangular loop antenna 48 that are not part of transmitter 24 but are referred to in the explanation below. Loop antenna 46 is of the same shape and size as loop antenna 30, and overlaps the halves of loop antennas 26 and 28 that are not overlapped by loop antenna 30. Loop antenna 48 matches the outer perimeter defined by loop antennas 26 and 28.

To understand the preferred mode of the operation of the system of the present invention, it is helpful to consider first a less preferred mode, based on time domain multiplexing, of operating a similar system that includes all five loop antennas of FIG. 6. In this less preferred mode, loop antenna 48 is energized using a sinusoidal current of angular frequency $\omega_1$. Then, loop antennas 26 and 28 are energized by oppositely directed sinusoidal currents of angular frequency $\omega_1$. Finally, loop antennas 30 and 46 are energized by oppositely directed sinusoidal currents of angular frequency $\omega_1$. The idea of this energization sequence is to produce, first, a field above the transmitter that is spatially symmetric in both the horizontal and the vertical direction as seen in FIG. 6, then a field above the transmitter that is antisymmetric in the horizontal direction and symmetric in the vertical direction, and finally a field that is symmetric in the horizontal direction and antisymmetric in the vertical direction. These three fields are linearly independent, and all three fields have significant amplitude all the way across the transmitter. The signals output by the three sensors of receiver 14 in response to the electromagnetic waves so generated are sampled at times $t_m$ by reception circuitry 34. The sampled signals are:

$s^o_{im} = c^o_{i,1} \cos \omega_1 t_m + c^o_{i,2} \sin \omega_1 t_m$ from loop antenna 48

$s^h_{im} = c^h_{i,1} \cos \omega_1 t_m + c^h_{i,2} \sin \omega_1 t_m$ from loop antenna 26 and 28

$s^v_{im} = c^v_{i,1} \cos \omega_1 t_m + c^v_{i,2} \sin \omega_1 t_m$ from loop antenna 30 and 46 where i indexes the sensor that receives the corresponding signal. Coefficients $c^o_{i,1}$, $c^h_{i,1}$ and $c^v_{i,1}$ are the in-phase amplitudes of the received signals. Coefficients $c^o_{i,2}$, $c^h_{i,2}$ and $c^v_{i,2}$ are the quadrature amplitudes of the received signals. Because $\omega_1$ is sufficiently low that receiver 14 is in the near fields generated by the loop antennas, in principle the quadrature amplitudes should be identically zero. Because of inevitable phase distortions, for example in reception circuitry 34, the quadrature amplitudes generally are not zero.

Note that amplitudes $c^o_{i,j}$, $c^h_{i,j}$ and $c^v_{i,j}$ (j=1,2) could be obtained by using only loop antennas 26, 28 and 30. The sampled signals obtained by energizing loop antennas 26, 28 and 30 separately with identical sinusoidal currents of angular frequency $\omega_1$ are:

$s^1_{im} = c^1_i \cos \omega_1 t_m + c^2_i \sin \omega_1 t_m$ from loop antenna 26

$s^2_{im} = c^3_i \cos \omega_1 t_m + c^4_i \sin \omega_1 t_m$ from loop antenna 28

$s^3_{im} = c^5_i \cos \omega_1 t_m + c^6_i \sin \omega_1 t_m$ from loop antenna 30 the coefficients $c^1_i$, $c^3_i$ and $c^5_i$ being in-phase amplitudes and the coefficients $c^2_i$, $c^4_i$ and $c^6_i$ being quadrature amplitudes. Because the field radiated by loop antennas 26 and 28 when identical currents J flow therein is the same as the field generated by loop antenna 48 when current J flows therein, $$c^o_{i,1} = c^1_i + c^3_i \quad (1)$$

$$c^o_{i,2} = c^2_i + c^4_i \quad (2)$$

By definition, $$c^h_{i,1} = c^1_i - c^3_i \quad (3)$$

$$c^h_{i,2} = c^2_i - c^4_i \quad (4)$$

Finally, the fact that the field radiated by loop antenna 48 could also be emulated by identical currents flowing through loops 30 and 46 gives $$c^v_{i,1} = 2c^5_i - c^1_i - c^3_i \quad (5)$$

$$c^v_{i,2} = 2c^6_i - c^2_i - c^4_i \quad (6)$$

In the preferred mode of the operation of the system of the present invention, loop antennas 26, 28 and 30 are energized simultaneously with sinusoidal currents of angular frequencies $\omega_1$, $\omega_2$ and $\omega_3$, respectively. The sampled signals now are $$s_{im} = c_{i1} \cos \omega_1 t_m + c_{i2} \sin \omega_1 t_m + c_{i3} \cos \omega_2 t_m + c_{i4} \sin \omega_2 t_m + c_{i5} \cos \omega_3 t_m + c_{i6} \sin \omega_3 t_m \quad (7)$$

Note that now, amplitudes $c_{i1}$ and $c_{i2}$ refer to frequency $\omega_1$, amplitudes $c_{i3}$ and $c_{i4}$ refer to frequency $\omega_2$, and amplitudes $c_{i5}$ and $c_{i6}$ refer to frequency $\omega_3$. The sampled signals are organized in a matrix s of three rows, one row for each sensor of receiver 14, and as many columns as there are times $t_m$, one column per time. Amplitudes $c_{ij}$ are organized in a matrix c of three rows and six columns. The matrices s and c are related by a matrix A of six rows and as many columns as there are in matrix s:

$$s = cA \tag{8}$$

Almost always, there are many more than six columns in matrix s, making equation (8) highly overdetermined. Because the transmission frequencies and the reception times are known, matrix A is known. Equation (8) is solved by right-multiplying both sides by a right inverse of matrix A: a matrix, denoted as $A^{-1}$, such that $AA^{-1}=I$, where I is the 6×6 identity matrix. Right inverse matrix $A^{-1}$ is not unique. A particular right inverse matrix $A^{-1}$ may be selected by criteria that are well known in the art. For example, $A^{-1}$ may be the right inverse of A of smallest $L^2$ norm. Alternatively, matrix c is determined as the generalized inverse of equation (8):

$$c = sA^T(AA^T)^{-1} \tag{9}$$

where the superscript "T" means "transpose". The generalized inverse has the advantage of being an implicit least squares solution of equation (8).

In the special case of evenly sampled times $t_m$, solving equation (8) is mathematically equivalent to the cross-correlation of WO 96/05768. Equation (8) allows the sampling of the signals from receiver 14 at irregular times. Furthermore, there is no particular advantage to using frequencies $\omega_1$, $\omega_2$ and $\omega_3$ that are integral multiples of a base frequency. Using closely spaced frequencies has the advantage of allowing the use of narrow-band filters in reception circuitry 34, at the expense of the duration of the measurement having to be at least about $2\pi/\Delta\omega$, where $\Delta\omega$ is the smallest frequency spacing, except in the special case of two signals of the same frequency and different phases.

Because receiver 14 is in the near field of transmitter 24, coefficients $c_{ij}$ of equation (7) are the same as coefficients $c'_{ij}$. It follows that equations (1)–(6) still hold, and either of two 3×3 matrices M can be formed from the elements of matrix c for further processing according to the description in co-pending Israel Patent Application 122578, an in-phase matrix $$M = \begin{pmatrix} c_{1,1}^0 & c_{1,1}^h & c_{1,1}^v \\ c_{2,1}^0 & c_{2,1}^h & c_{2,1}^v \\ c_{3,1}^0 & c_{3,1}^h & c_{3,1}^v \end{pmatrix} \tag{10}$$

or a quadrature matrix $$M = \begin{pmatrix} c_{1,2}^0 & c_{1,2}^h & c_{1,2}^v \\ c_{2,2}^0 & c_{2,2}^h & c_{2,2}^v \\ c_{3,2}^0 & c_{3,2}^h & c_{3,2}^v \end{pmatrix} \tag{11}$$

Note that because the system of the present invention is a closed-loop system, there is no sign ambiguity in M, unlike the corresponding matrix of co-pending Israel Patent Application 122578.

Let T be the orthonormal matrix that defines the rotation of probe 10 relative to the reference frame of transmitter 24. Write M in the following form:

$$M = ET_0T \tag{12}$$

where $T_0$ is an orthogonal matrix and E is in general a nonorthogonal matrix. In general, $T_0$ and E are functions of the position of probe 10 relative to the reference frame of transmitter 24. Let $$W^2 = MM^T = ET_0TT^TT_0^TE^T = EE^T \tag{13}$$

$W^2$ is real and symmetric, and so can be written as $W^2 = Pd^2P^T = (PdP^T)^2$, where $d^2$ is a diagonal matrix whose diagonal elements are the (real and positive) eigenvalues of $W^2$ and where P is a matrix whose columns are the corresponding eigenvectors of $W^2$. Then $W = PdP^T = E$ also is symmetric. Substituting in equation (12) gives:

$$M = PdP^TT_0T \tag{14}$$

so that $$T = T_0^TPd^{-1}P^TM \tag{15}$$

If $T_0$ is known, then T, and hence the orientation of probe 10 with respect to the reference frame of transmitter 24, can be computed using equation (15).

For any particular configuration of the antennas of transmitter 24, $T_0$ may be determined by either of two different calibration procedures.

In the experimental calibration procedure, probe 10 is oriented so that T is a unit matrix, probe 10 is moved to a succession of positions relative to transmitter 24, and M is measured at each position. The equation $$T_0 = Pd^{-1}P^TM \tag{16}$$

gives $T_0$ at each of those calibration positions.

There are two variants of the theoretical calibration procedure, both of which exploit reciprocity to treat receiver 14 as a transmitter and transmitter 24 as a receiver. The first variant exploits the principle of reciprocity. The sensor elements are modeled as point sources, including as many terms in their multipole expansions as are necessary for accuracy, and their transmitted magnetic fields in the plane of transmitter 24 are calculated at a succession of positions relative thereto, also with probe 10 oriented so that T is a unit matrix. The EMF induced in the antennas of transmitter 24 by these time-varying magnetic fields is calculated using Faraday's law. The transfer function of reception circuitry 34 then is used to compute M at each calibration position, and equation (16) gives $T_0$ at each calibration position. In the second variant, the magnetic field generated by each antenna of transmitter 24 at the three frequencies $\omega_1$, $\omega_2$ and $\omega_3$ is modeled using the Biot-Savart law. Note that each frequency corresponds to a different sensor 16, 18 or 20. The signal received at each sensor is proportional to the projection of the magnetic field on the sensitivity direction of the sensor when object 10 is oriented so that T is a unit matrix. This gives the corresponding column of M up to a multiplicative constant and up to a correction based on the transfer function of reception circuitry 34.

To interpolate $T_0$ at other positions, a functional expression for $T_0$ is fitted to the measured values of $T_0$. Preferably, this functional expression is a polynomial. It has been found most preferable to express the Euler angles $\alpha$, $\beta$ and $\gamma$ that define $T_0$ as the following 36-term polynomials. The arguments of these polynomials are not direct functions of Cartesian coordinates x, y and z, but are combinations of certain elements of matrix W that resemble x, y and z, specifically, $a = W_{13}/(W_{11}+W_{33})$, which resembles x; $b = W_{23}/(W_{22}+W_{33})$, which resembles y, and $c = \log(1/W_{33})$, which resembles z. Using a direct product notation, the 36-term polynomials can be expressed as:

$$\alpha = (a, a^3, a^5)(b, b^3, b^5)(1, c, c^2, c^3)AZcoe \tag{17}$$

$$\beta=(a, a^3, a^5)(1, b^2, b^4, b^6)(1, c, c^2)ELcoe \quad (18)$$

$$\gamma=(1, a^2, a^4, a^6)(b, b^3, b^5)(1, c, c^2)RLcoe \quad (19)$$

where AZcoe, ELcoe and RLcoe are 36-component vectors of the azimuth coefficients, elevation coefficients and roll coefficients that are fitted to the measured or calculated values of the Euler angles. Note that to fit these 36-component vectors, the calibration procedure must be carried out at at least 36 calibration positions. At each calibration position, W is computed from M using equation (13), and the position-like variables a, b and c are computed from W as above.

Similarly, the Cartesian coordinates x, y and z of probe 10 relative to the reference frame of transmitter 24 may be expressed as polynomials. It has been found most preferable to express x, y and z as the following 36-term polynomials:

$$x=(a, a^3, a^5)(1, b, b^4)(1, c, c^2, c^3)Xcoe \quad (20)$$

$$y=(1, a^2, a^4)(b, b^3, b^5)(1, c, c^2, c^3)Ycoe \quad (21)$$

$$z=(1, a^2, a^4)(1, b^2, b^4)(1, d, d^2, d^3)Zcoe \quad (22)$$

where Xcoe, Ycoe and Zcoe are 36-component vectors of the x-coefficients, the y-coefficients, and the z-coefficients, respectively; and d=log(c). As in the case of the Euler angles, these position coordinate coefficients are determined by either measuring or computing M at at least 36 calibration positions and fitting the resulting values of a, b and c to the known calibration values of x, y and z. Equations (17) through (22) may be used subsequently to infer the Cartesian coordinates and Euler angles of moving and rotating probe 10 noniteratively from measured values of M.

Although the antenna configuration illustrated in FIGS. 1 and 6 is the most preferred configuration, other configurations fall within the scope of the present invention. FIGS. 7A, 7B and 7C show three alternative configurations of paired adjacent loop antennas 26' and 28'. The arrows indicate the direction of current flow that emulates a single loop antenna coincident with the outer perimeter of antennas 26' and 28'. Other useful coplanar overlapping antenna configurations are described in PCT Publication No. WO 96/03188, entitled "Computerized game Board", which is incorporated by reference for all purposes as if fully set forth herein.

Figure 8:
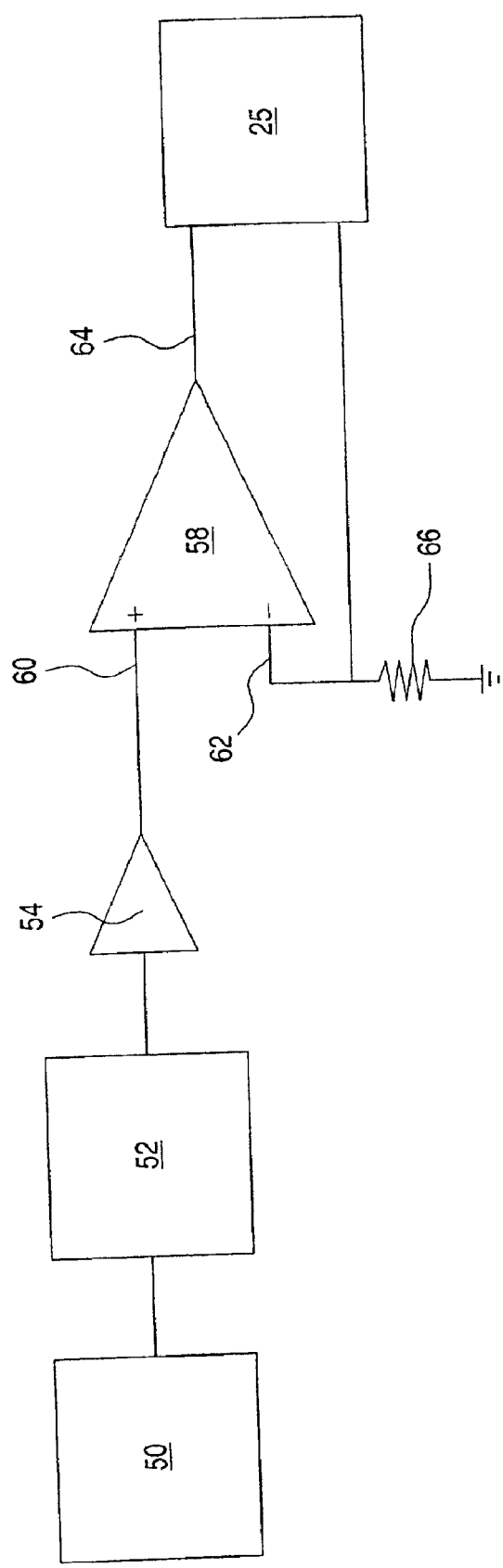
FIG. 8 is a schematic block diagram of driving circuitry

FIG. 8 is a schematic block diagram of driving circuitry 32 for driving a generic antenna 25 that represents any one of loop antennas 26, 28 or 30. A digital signal generator 50 generates samples of a sinusoid that are converted to an analog signal by a D/A converter 52. This analog signal is amplified by an amplifier 54 and sent to the positive input 60 of a differential amplifier 58. Loop antenna 25 is connected both to the output 64 of differential amplifier 58 and to the negative input 62 of differential amplifier 58. Negative input 62 also is grounded via a resistor 66. The feedback loop thus set up drives antenna 25 at the frequency of the sinusoid generated by signal generator 50, and makes antenna 25 appear to be an open circuit at all other frequencies.

Unlike the circuitry of WO 97/36143, which acts to offset the influence of one loop antenna on another, the circuitry of FIG. 8 decouples loop antenna 25 from the other loop antennas. The superiority of the present invention over WO 97/36143 is evident. Consider, for example, how WO 97/36143 and the present invention correct for the mutual inductances of loop antenna 26, radiating at a frequency $\omega_1$, and loop antenna 30, radiating at a frequency $\omega_2$. The goal is to set up the field of frequency $\omega_1$ that would be present if only loop antenna 26, and not loop antenna 30, were present, and to set up the field of frequency $\omega_2$ that would be present if only loop antenna 30, and not loop antenna 26, were present. By Faraday's and Ohm's laws, the time rate of change of the magnetic flux through loop antenna 26 is proportional to the current through loop antenna 26, and the time rate of change of the magnetic flux through loop antenna 30 is proportional to the current through loop antenna 30. In the absence of loop antenna 30, loop antenna 26 sets up a certain time-varying magnetic flux of frequency $\omega_1$ across the area that would be bounded by loop antenna 30 if loop antenna 30 were present. The method of WO 97/36143 forces the time rate of change of this magnetic flux through loop antenna 30 to be zero. Because the magnetic flux has no DC component, the magnetic flux itself through loop antenna 30 therefore also vanishes, which is contrary to the situation in the absence of loop antenna 30. By contrast, the present invention makes loop antenna 30 appear to be an open circuit at frequency $\omega_1$ and so does not change the magnetic flux from what it would be in the absence of loop antenna 30.

Figure 9:
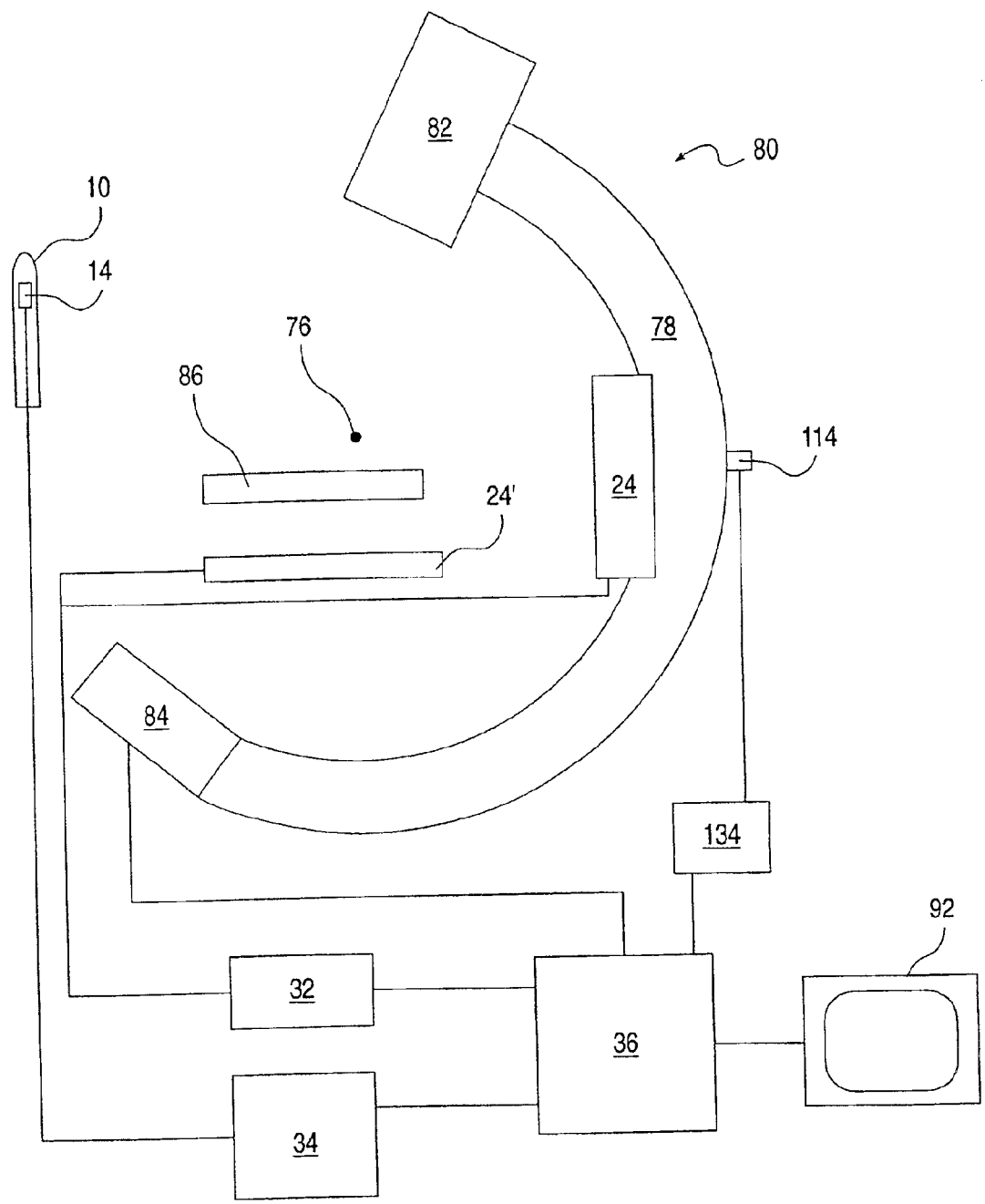
FIG. 9 shows a C-mount fluoroscope modified for real-time intrabody navigation

FIG. 9 shows, schematically, a C-mount fluoroscope 80 modified according to the present invention for simultaneous real-time image acquisition and intrabody navigation. Fluoroscope 80 includes the conventional components of a C-mount fluoroscope: an x-ray source 82 and an image acquisition module 84 mounted on opposite ends of a C-mount 78, and a table 86 whereon the patient lies. Image acquisition module 84 converting x-rays that transit the patient on table 86 into electronic signals representative of a 2D image of the patient. C-mount 78 is pivotable about an axis 76 to allow the imaging of the patient from several angles, thereby allowing the reconstruction of a 3D image of the patient from successive 2D images. In addition, either a receiver 114, similar to receiver 14, or transmitter 24, is rigidly mounted on C-mount 78. Receiver 114 or transmitter 24 serves to define a frame of reference that is fixed relative to C-mount 78. The other components shown in FIG. 1, i.e., driving circuitry 32, reception circuitry 34, and control/processing unit 36, are connected to transmitter 24 and to receiver 14 in probe 10 as described above in connection with FIG. 1. In addition, signals from receiver 114 that correspond to the electromagnetic waves generated by transmitter 24' are sent to reception circuitry 134 that is identical to reception circuitry 34, and controller/processor 36 directs the reception of received signals by reception circuitry 134 and the acquisition of an image of the patient by image acquisition module 84 of fluoroscope 80.

By determining the position and orientation of probe 10 relative to the frame of reference defined by transmitter 24, controller/processor 36 determines the position and orientation of probe 10 relative to each acquired 2D image. Alternatively, the electromagnetic signals are transmitted by a transmitter 24' that is not attached to C-mount 78, and controller/processor 36 determines the position and orientation of probe 10 relative to the 2D images by determining the positions and orientations of receivers 14 and 114 relative to transmitter 24'. Controller/processor 36 synthesizes a combined image that includes both the 3D image of the patient acquired by fluoroscope 80 and an icon representing probe 10 positioned and oriented with respect to the 3D image of the patient in the same way as probe 10 is positioned and oriented with respect to the interior of the patient. Controller/processor 36 then displays this combined image on a monitor 92.

C-mount fluoroscope 80 is illustrative rather than limitative. The scope of the present invention includes all suitable devices for acquiring 2D or 3D images of the interior of a patient, in modalities including CT, MRI and ultrasound in addition to fluoroscopy.

Figure 11:
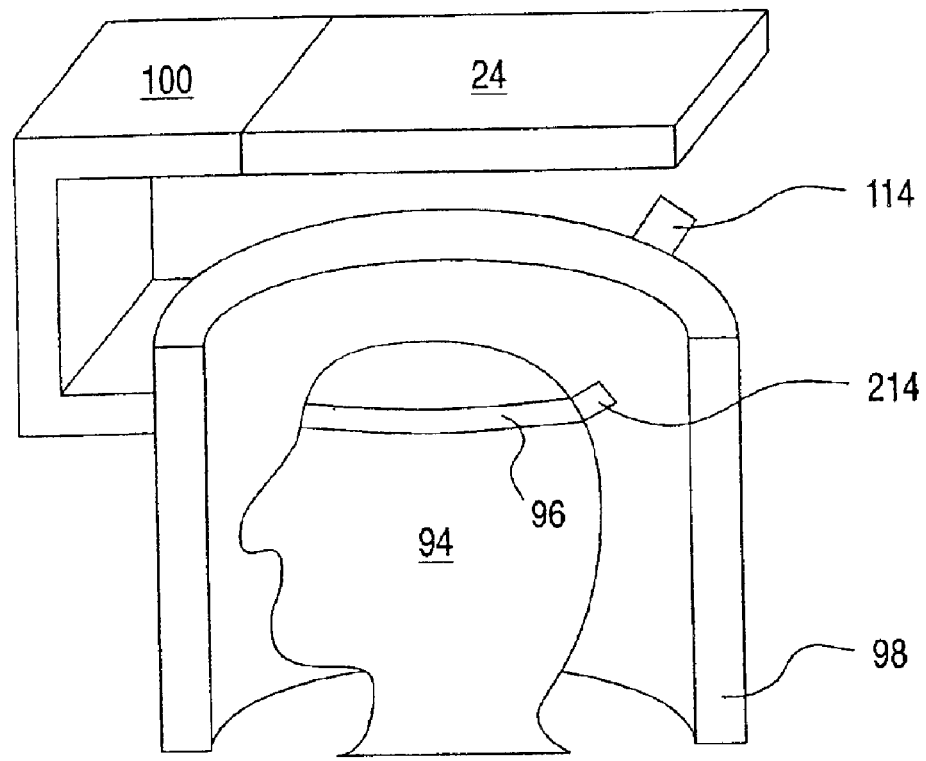
FIG. 11 shows a CT scanner modified for imaging in support of subsequent intracranial navigation.

Under certain circumstances, the image acquisition and the intrabody navigation may be done sequentially, rather than simultaneously. This is advantageous if the medical imaging facilities and the medical treatment facilities can not be kept in the same location. For example, the human skull is sufficiently rigid that if a receiver of the present invention is rigidly mounted on the head of a patient using an appropriate headband, then the position and orientation of the receiver is a sufficient accurate representation of the position and orientation of the patient's head to allow intracranial navigation. FIG. 11 shows a head 94 of a patient inside a (cut-away) CT scanner 98. As in the case of fluoroscope 80 of FIG. 9, receiver 114 and transmitter 24 are rigidly attached to CT scanner 98, transmitter 24 being so attached via an arm 100. CT scanner 98 acquires 2D x-ray images of successive horizontal slices of head 94. A receiver 214 is rigidly mounted on head 94 using a headband 96. As the 2D images are acquired, the position and orientation of receiver 214 with respect to each image is determined by the methods described above for determining the position and orientation of probe 10 with respect to the 2D images acquired by fluoroscope 80. These positions and orientations are stored, along with the 2D images, in control/processing unit 36. Subsequently, during medical treatment of head 94 that requires navigation of probe 10 through head 94, the position and orientation of probe 10 in head 94 is determined using signals from receivers 14 and 214 in the manner described above for positioning and orienting probe 10 with respect to C-mount 78 of fluoroscope 80 using receivers 14 and 114. Given, now, for each 2D CT image, the position and orientation of probe 10 with respect to receiver 214 and the position and orientation of receiver 214 with respect to that 2D image, it is trivial to determine the position and orientation of probe 10 with respect to that 2D image. As in the case of the simultaneous imaging and navigation depicted in FIG. 9, controller/processor 36 now synthesizes a combined image that includes both the 3D image of head 94 acquired by CT scanner 98 and an icon representing probe 10 positioned and oriented with respect to the 3D image of head 94 in the same way as probe 10 is positioned and oriented with respect to head 94. Controller/processor 36 then displays this combined image on monitor 92.

As in the case of fluoroscope 80, CT scanner 98 is illustrative rather than limitative. The scope of the present invention includes all suitable devices for acquiring 2D or 3D images of a limb of a patient, in modalities including MRI, ultrasound and fluoroscopy in addition to CT. Note that this method of image acquisition followed by intrabody navigation allows the a centrally located imaging device to serve several medical treatment facilities.

Figure 14:
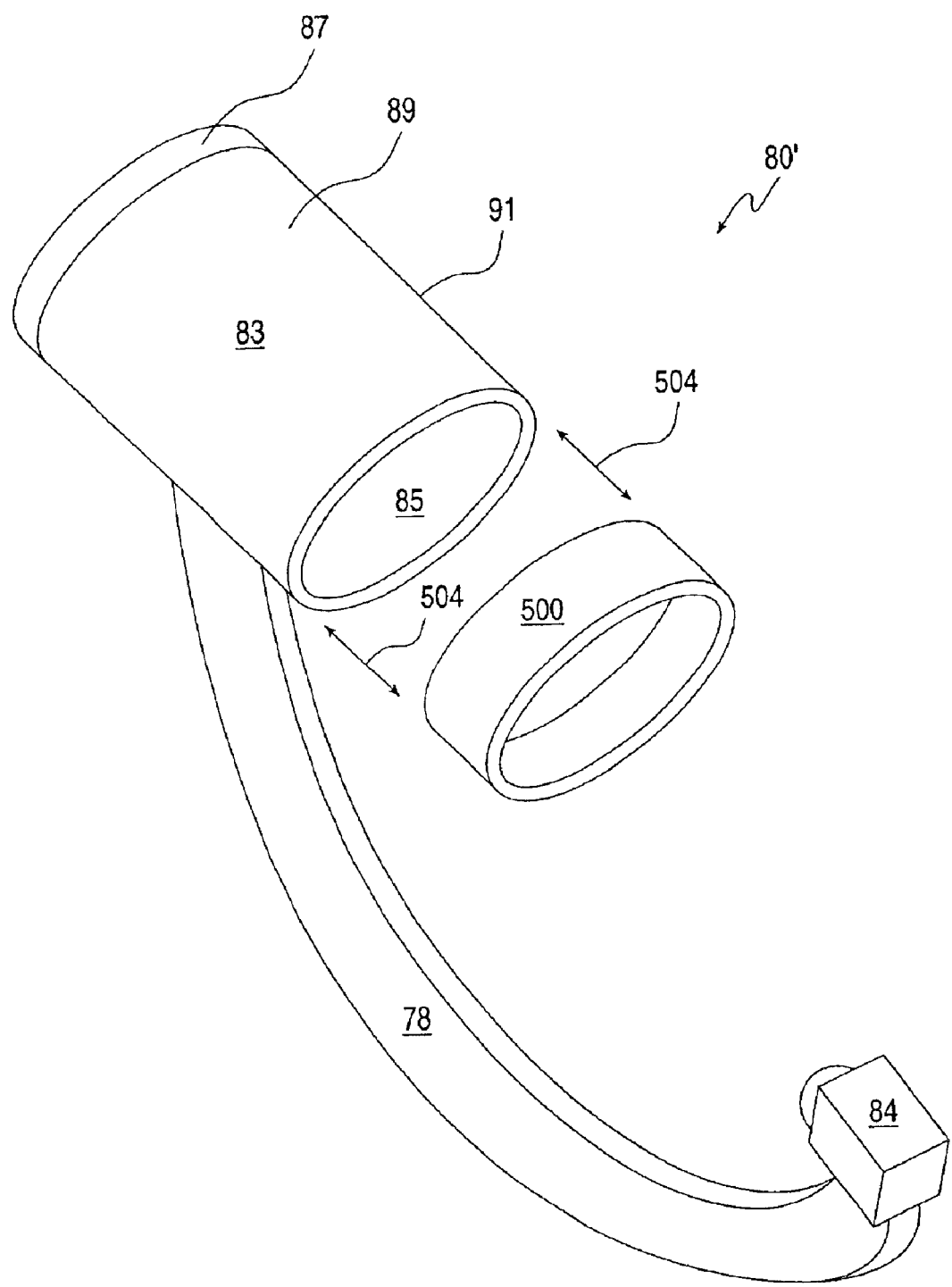
FIG. 14 is a partial perspective view of the C-mount fluoroscope of FIG. 9, including a magnetically permeable compensator.

FIG. 14 is a partially exploded, partial perspective view of a C-mount fluoroscope 80' modified according to one aspect of the present invention. Like C-mount fluoroscope 80, C-mount fluoroscope 80' includes an x-ray source 84 and an image acquisition module 82 at opposite ends of a C-mount 78. Image acquisition module 82 includes an image intensifier 83, a front face 85 whereof faces x-ray source 84, and a CCD camera 87, mounted on the end of image intensifier 83 that is opposite front face 85, for acquiring images that are intensified by image intensifier 83. Image intensifier 83 is housed in a cylindrical housing 91. In addition, fluoroscope 80' includes an annular compensator 500 made of a magnetically permeable material such as mu-metal.

The need for compensator 500 derives from the fact that front face 85 is electrically conductive. The electromagnetic waves generated by transmitter 24 or 24' induce eddy currents in front face 85 that distort the electromagnetic field sensed by receiver 14. Placing a mass of a magnetically permeable substance such as mu-metal in the proper spatial relationship with front face 85 suppresses this distortion. This is taught, for example, in U. S. Pat. No. 5,760,335, to Gilboa, which patent is incorporated by reference for all purposes as if fully set forth herein, in the context of shielding a CRT from external radiation without perturbing the electromagnetic field external to the CRT.

Preferably, compensator 500 is a ring, 5 cm in axial length, of mu metal foil 0.5 mm thick. Compensator 500 is slidably mounted on the external surface 89 of cylindrical housing 91, as indicated by double-headed arrows 504, and is held in place by friction. It is straightforward for one ordinarily skilled in the art to select a position of compensator 500 on housing 91 that provides the optimal suppression of distortions of the electromagnetic field outside image intensifier 83 due to eddy currents in front face 85.

It often is desirable to retrofit a new apparatus such as receiver 14 to an existing catheter rather than to design a new probe 10 that includes both the new apparatus and the functionality of an already existing probe. This retrofit capability is particularly important if probe 10 would have been used for medical applications, and both the apparatus and the existing probe had already been approved for medical applications by the relevant regulatory bodies. Such a retrofit capability then would preclude the need to obtain regulatory approval for the new probe, a process that often is both expensive and time-consuming.

FIG. 16 illustrates just such a retrofit capability, for adapting a satellite 550 to a substantially cylindrical catheter 552 for invasively probing or treating a body cavity such as a chamber of the heart. Satellite 550 is an instrumentation capsule that may contain receiver 14 or any other medically useful apparatus. For example, satellite 550 may contain an apparatus for ablating cardiac tissue. A catheter such as catheter 552 is introduced to the body cavity of a patient via the patient's blood vessels, via an introducer sheath. It is important that the external diameter of the introducer sheath be minimized, to reduce the risk of bleeding by the patient. Consequently, the external diameter of catheter 552 also must be minimized, and any scheme for retrofitting satellite 550 to catheter 552 must allow satellite 550 to be introduced into the introducer sheath along with catheter 552. It is the latter requirement that generally precludes simply attaching satellite 550 to catheter 552. In addition, if satellite 550 includes receiver 14, with the intention of using receiver 14 to track the position and orientation of catheter 550, then, when satellite 550 and catheter 552 are deployed within the body cavity, satellite 550 must have a fixed position and orientation relative to catheter 552.

The retrofitting scheme of FIG. 16 achieves these ends by providing satellite 550 and catheter 552 with a mechanism for providing only a loose mechanical connection between satellite 550 and catheter 552 as satellite 550 and catheter 552 are introduced to the body cavity, and only then securing satellite 550 to catheter 552 at a fixed position and orientation relative to catheter 552. FIG. 16A shows a thin flexible tether 554 attached to proximal end 556 of satellite 550. Tether 554 provides a mechanical link to the outside of the patient. Depending on the instrumentation installed in tether 554, tether 554 may also provide a communications link to the outside of the patient. For example, if satellite 550 includes receiver 14, then extensions of wire pairs 38 are included in tether 554. Rigidly attached to tether 554 is a hollow cylindrical sleeve 558 whose inner diameter is the same as the outer diameter of catheter 552.

The remainder of the mechanism for reversibly securing satellite 550 to catheter 552 is shown in FIG. 16B. Catheter 552 is provided, near distal end 564 thereof, with a pocket 560 made of a flexible, resilient, elastic material. Pocket 560 is attached rigidly to the outer surface of catheter 552. Pocket 560 includes an aperture 562, which is adjacent catheter 552 at the proximal end of catheter 552, and which accommodates tether 554. Pocket 560 is sized to accommodate satellite 550 snugly therein via an opening in distal end 566 of pocket 560.

Satellite 550, catheter 552 and the associated securing mechanism are assembled as shown in FIG. 16C, with tether 554 running through aperture 562, sleeve 558 encircling catheter 552 proximal of pocket 560, and satellite 550 distal of pocket 560. Catheter 552 and tether 554 are shown emerging from the distal end of a protective jacket 568. Preferably, sleeve 558 is made of a low-friction material such as Teflon™, to allow sleeve 558 to slide freely along catheter 552. The assembly shown in FIG. 16C is introduced to the introducer sheath with satellite 550 in front of catheter 552. During this introduction, pocket 560 is compressed against the outer surface of catheter 552 by the introducer sheath. Tether 554 is sufficiently flexible to bend along with catheter 552 and jacket 568 as the assembly shown in FIG. 16C passes through the patient's blood vessels, but is sufficiently rigid to push satellite 550 ahead of distal end 564 of catheter 552 as catheter 552 is inserted into the patient. As a result, satellite 550 and distal end 564 of catheter 552 reach interior of the targeted body cavity in the configuration illustrated in FIG. 16C. At this point, pocket 560 opens, and tether 554 is pulled to withdraw satellite 550 into pocket 560 via the opening in distal end 566 of pocket 560. Satellite 550 and tether 554 now are held by pocket 560, sleeve 558 and jacket 568 in a fixed position and orientation relative to catheter 552, as illustrated in FIG. 16D.

Subsequent to treatment, tether 554 is pushed to restore the configuration shown in FIG. 16C, to allow catheter 552 and satellite 550 to be withdrawn from the patient.

While the invention has been described with respect to a limited number of embodiments, it will be appreciated that many variations, modifications and other applications of the invention may be made.

What is claimed is:

1. A catheter, comprising:

(a) a housing having a transverse inner dimension of at most about two millimeters; and (b) a coil arrangement including at least five coils and at least five solid cores, each of said coils being wound around one of said cores, said coils being non-coaxial, said coil arrangement being mounted inside said housing.

2. The catheter of claim 1, wherein said solid cores includes ferrite.

3. The catheter of claim 1, wherein said coils have an axis, said axes of at least three of said coils being substantially mutually perpendicular to each other.

4. The catheter of claim 1, wherein each of said coils has a center, said centers of said coils lying on a substantially straight line.

5. A probe for interacting with a body cavity, comprising:

(a) a substantially cylindrical catheter;

(b) a satellite; being part of a sensing probe;

(c) a flexible pocket having an aperture therein, said flexible being rigidly, attached to said catheter, said flexible pocket being configured for receiving said satellite therein; and (d) a tether passing through said aperture, said tether being attached to said satellite, such that, after said catheter and said satellite have been inserted into the body cavity, said tether is withdrawn, thereby pulling said satellite into said flexible pocket so as to reversibly secure said satellite at a fixed position and orientation relative to said catheter.

6. The probe of claim 5, wherein said mechanism includes:

(i) a sleeve, rigidly secured to said tether and adapted to slide along said catheter.

7. The probe of claim 5, wherein said sensor is configured for sensing a position and orientation of said catheter.

* * * * *

UNITED STATES PATENT AND TRADEMARK OFFICE
CERTIFICATE OF CORRECTION

PATENT NO. : 6,947,788 B2
DATED : September 20, 2005
INVENTOR(S) : Gilboa et al.

It is certified that error appears in the above-identified patent and that said Letters Patent is hereby corrected as shown below:

Column 24,
Line 8, insert -- solid -- between "one of said..... cores".
Line 22, delete ";" after "satellite".
Line 24, insert -- pocket -- after "flexible" and delete ";" after "rigidly".

Signed and Sealed this

Twenty-first Day of February, 2006

JON W. DUDAS
*Director of the United States Patent and Trademark Office*